United States Patent [19]

Graham et al.

[11] Patent Number: 5,132,463

[45] Date of Patent: Jul. 21, 1992

[54] 1,3-DIARYL CYCLOPENTANES AND DERIVATIVES THEREOF AS PAF ANTAGONISTS

[75] Inventors: Donald W. Graham, Mountainside; John C. Chabala, Westfield; Tesfaye Biftu, Parlin, all of N.J.; Michael N. Chang, Newtown, Pa.; Yuan-Ching P. Chiang, Piscataway, N.J.; Shu S. Yang, Bridgewater, N.J.; Kathryn L. Thompson, Westfield, N.J.

[73] Assignee: Merck & Co., Inc., Rahway, N.J.

[21] Appl. No.: 713,895

[22] Filed: Jun. 12, 1991

Related U.S. Application Data

[60] Division of Ser. No. 396,489, Aug. 21, 1989, Pat. No. 5,047,420, which is a continuation-in-part of Ser. No. 88,320, Aug. 24, 1987, abandoned, and Ser. No. 898,966, Aug. 21, 1986, abandoned.

[51] Int. Cl.$^5$ .................. C07C 317/14; C07C 317/22
[52] U.S. Cl. ........................ 568/33; 568/29; 568/34
[58] Field of Search ............... 568/33, 330, 29, 34; 514/708, 709, 717, 719

[56] References Cited

U.S. PATENT DOCUMENTS 4,845,129  7/1989  Anderson et al. ............ 514/708
5,047,420  9/1991  Graham ........................... 568/33

OTHER PUBLICATIONS

P. Ruggli et al., J.O.C., 26, 307 (1961).
Strashneuko et al., 2h Org. Khim., 3, 91 (1967).
D. H. Richards et al., J. Chem. Soc. (c) 2661 (1969).

Primary Examiner—Marianne Cintins
Assistant Examiner—John Peabody
Attorney, Agent, or Firm—Curtis C. Panzer; Hesna J. Pfeiffer

[57] ABSTRACT

Novel 1,3-Diaryl cyclopentanes of the following general formula were prepared.

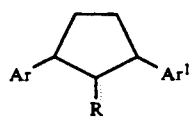

(I)

These compounds were found to have potent and specific PAF (Platelet Activating Factor) antagonistic activities and as such useful in the treatment or amelioration of various diseases or disorders mediated by the PAF, for example, hypotension, inflammation, nephritis, stroke and other cardiovascular disorders, asthma, allergic and skin diseases, peptic or stomach ulcer, shock, lung edema, psoriasis, adult respiratory distress syndrome, pain including dental pain, and aggregation of platelets.

8 Claims, No Drawings

1,3-DIARYL CYCLOPENTANES AND DERIVATIVES THEREOF AS PAF ANTAGONISTS

This application is a division of application Ser. No. 396,489, filed Aug. 21, 1989, now U.S. Pat. No. 4,047,420 which is a continuation-in-part of U.S. Ser. No. 088,320, filed Aug. 24, 1987 now abandoned and U.S. Ser. No. 898,966 filed Aug. 21, 1986, now abandoned.

BACKGROUND OF THE INVENTION

Platelet-activating factor (PAF) has recently been identified as an acetyl glyceryl ether phosphorylcholine (AGEPC), i.e., 1-0-hexadecyl/octadecyl-2-acetyl-sn-glyceryl-3-phosphorycholine (Hanahan D. J., et al., *J. Biol. Chem.* 255:5514, 1980). Even before its chemical identification, PAF had been linked to various biological activities and pathways making it one of the important mediators responsible for a variety of physiological processes including activation or coagulation of platelets, pathogenesis of immune complex deposition, smooth muscle contraction, inflammation, hypotension, shock, pain, edema as well as respiratory, cardiovascular, renal and intravascular alterations. Since these physiological processes are in turn associated with a large group of diseases, for example, inflammatory disease, nephritis, stroke and other cardiovascular disorders, hypotension, shock, psoriasis, allergic and skin diseases, asthma, lung edema, peptic or stomach ulcer, dental pain, and adult respiratory distress syndrome, more and more scientific investigation has been focused on the search of a PAF antagonist or inhibitor for treating or preventing these common diseases.

The compounds of the present invention are specific PAF antagonists which can exist in various isomers. For example, the cyclopentane derivatives of formula (A) can exist in four different stereo-isomers as shown in Scheme I. Each stereoisomers in turn exists in a pair of ±enantiomers.

Scheme I

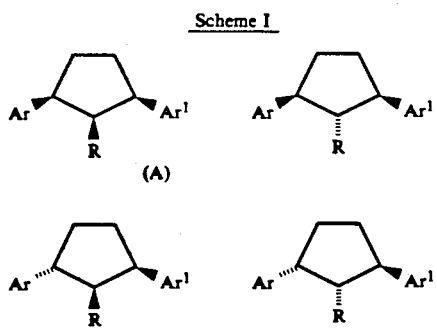

These isomers bear a close relationship to the PAF antagonistic activity observed for the compounds within the scope of this invention.

Accordingly, it is the object of the present invention to prepare the most potent isomers of known or novel cyclopentane derivatives as PAF antagonists and use them for the treatment of various diseases including prevention of platelet aggregation, hypotension, inflammation, asthma, lung edema, adult respiratory distress syndrome, various shock syndromes, cardiovascular disorders and other related skeletal-muscular disorders.

Another object of the present invention is to develop processes for the preparation of the 1,3-diarylcyclopentane derivatives.

A further object of the present invention is to provide acceptable pharmaceutical compositions containing one or more of the cyclopentane derivatives as the active ingredient. As PAF antagonists, these novel compositions should be effective in the treatment of various PAF-induced diseases.

Finally, it is the object of this invention to provide a method of treatment comprising the administration of a therapeutically sufficient amount of these PAF antagonists to a patient suffering from various disorders including inflammation, e.g., osteoarthritis, rheumatoid arthritis, gout, and nephritis, hypotension, shock, psoriasis, allergic or skin diseases, asthma, pain especially dental pain, peptic or stomach ulcer, lung edema, adult respiratory distress syndrome or stroke and other cardiovascular disorders.

DETAILED DESCRIPTION OF THE INVENTION

A. Scope of the Invention

This invention relates to PAF antagonists of the structural formula (I)

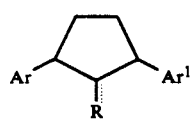

(I)

wherein
R is
(a) when R is connected to the cyclopentane ring by a single bond:
   (1) $-(X)_m(CH_2)_nR^1$ wherein X is O, $NR^2$, $NR^2R^3$, S, SO, $SO_2$, $SO_3$ or CO; m is 0 or 1; n is 1-6; $R^1$, $R^2$, $R^3$ are as defined below;
   (2) $-X^2R^2$ wherein $X^2$ is SO, $SO_2$, $SO_3$, $SO_2NR^3$, $NR^3(CO)$, $NR^3(CO)NH$, or $NHSO_2$; or
   (3) $R^1$;
(b) when R is connected to the cyclopentane ring by a double bond:
   (1) $=CR^2$;
   (2) $=O$; or
   (3) $=NOR^2$;
$R^1$ is
(a) H;
(b) loweralkyl or hydroxy substituted lower alkyl especially where the lower alkyl is $C_{1-8}$ alkyl, e.g., methyl, ethyl, isopropyl, n-propyl, n-butyl, t-butyl, pentyl, hexyl, heptyl or octyl;
(c) loweralkenyl especially $C_{2-8}$ alkenyl, e.g. vinyl, allyl, $CH_3CH=CHCH_2CH_2-$, $CH_3(CH_2)_3CH=CH-$ and $(CH_3)_2C=CH-$;
(d) lowercycloalkyl especially $C_{3-8}$ cycloalkyl;
(e) loweralkynyl especially $C_{2-8}$ alkynyl, e.g., $-C\equiv CH$;
(f) $-(CO)NR^2R^3$ wherein $R^2$ and $R^3$ independently are H, $C_{1-8}$ alkyl, $C_{3-8}$ cycloalkyl, e.g., cyclopropyl, cyclopentyl and cyclohexy, or $C_{1-4}$ perhaloalkyl such as $CF_3-$;
(g) $-(CO)R^2$;
(h) $-S(O)_qR^2$ where q represents 0-2;
(i) $-O(CO)R^2$;
(j) $-SO_2NR^2R^3$;

(k) —NR²(CO)R³;
(l) —NR²(CO)NHR³;
(m) —NHSO₂R²;
(n) —OR²
(o) —NR²R³;
(p) —CN;
(q) —NO₂
(r) halo e.g., Cl, F, Br and I;
(s) perhalo $C_{1-6}$ alkyl, e.g., —CF₃;
(t) phenyl or substituted phenyl as defined below; or
(u) —(CO)OR²;

Ar and Ar¹ are the same or different from each other and are (a) phenyl or substituted phenyl or formula

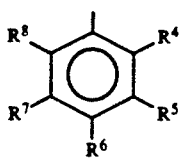

wherein $R^4$-$R^8$ independently represent H; R²; YO— wherein Y is R², loweralkenyl such as —CH₂—CH=CH₂; loweralkenyl such as —CH—C≡CH,

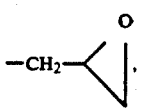

—CH₂—C(O)OR², —CH₂—OR², —CH₂C₃₋₈-cycloalkyl such as

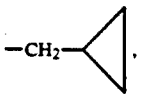

—CH₂Ar² wherein Ar² is phenyl or substituted phenyl, NR²SO₂R³; COR²; NO₂; CN; or $R^4$-$R^5$, $R^5$-$R^6$, $R^6$-$R^7$ and $R^7$-$R^8$ joined together and form a ring, for example, —OCH₂O—, —OCH₂CH₂—O— or —OCH₂CH₂N—. The representative phenyl groups can be 3-methoxy-4-methyl-thiophenyl, 4-trifluoromethoxyphenyl, 3-methoxy-4-trifluoromethoxy phenyl, 3,4-dimethoxyphenyl, 3-methoxy-4-dimethylaminophenyl, and 3,4,5-trimethoxyphenyl;

(b) monoheteroaryl, di- or polyheteroaryl, or fused heteroaryl containing from 1 to 3 of any one or more of the heteroaryl ring thereof and each ring may either be unsubstituted or substituted appropriately with a radical selected from a group consisting of $R^4$-$R^8$, for example, pyridyl, pyrryl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbozolyl, and isoxazolyl and the like.

The following are the preferred heteroaryl groups:
(1) pyrryl or pyrryl substituted with $R^4$-$R^6$;
(2) furyl or furyl substituted with $R^4$-$R^6$;
(3) pyridyl or pyridyl substituted with $R^4$-$R^7$;
(4) thiophene or thiophene substituted with $R^4$-$R^6$;
(5) thiazolyl or thiazolyl substituted with $R^4$-$R^5$; or
(6) pyrimidyl or pyrimidyl substituted with $R^4$-$R^6$.

In one embodiment, the PAF antagonists of this invention are of structural formula

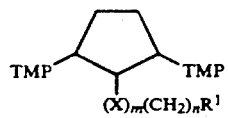

or an isomer thereof wherein TMP is 3,4,5-trimethoxyphenyl.

In another embodiment this invention involves compounds of structural formula

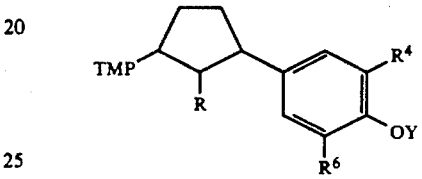

Still another embodiment of this invention involves compounds of formula

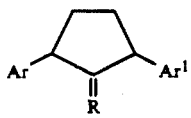

wherein R is NOR² or O; and Ar¹ is TMP or

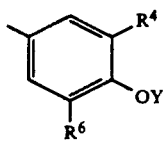

B. Preparation of the Compounds Within the Scope of the Invention

The PAF antagonists of this invention have been prepared largely by reductions of appropriately substituted cyclopentanones of their corresponding hydrazone derivatives:

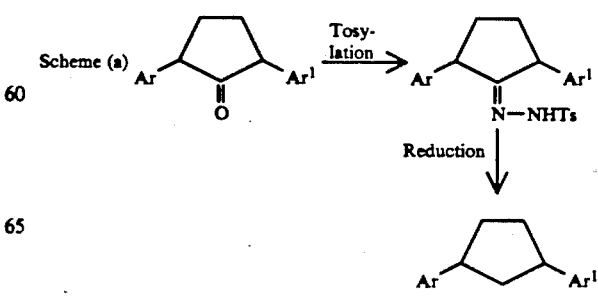

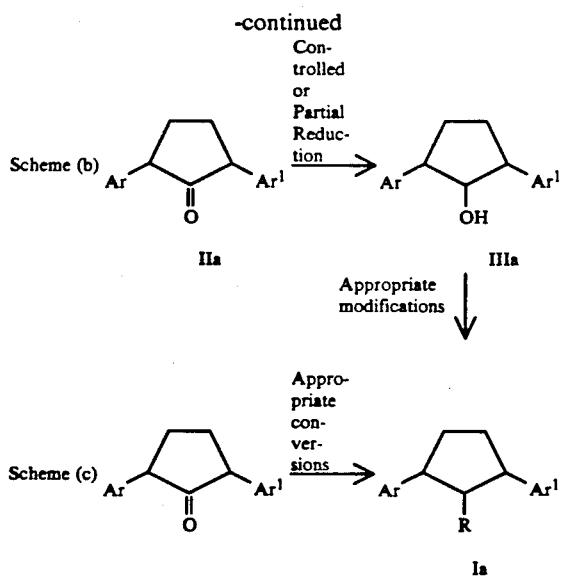

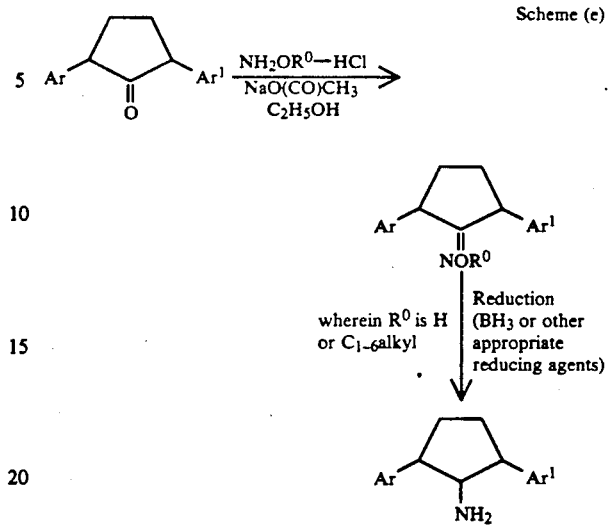

According to Scheme (a), the cyclopentanone derivative II is first converted to the tosylhydrazone derivative IIb which in turn is reduced under mild temperatures (about 50° C. to 150° C.) by NaBH₃CN in dimethylformamide (DMF) and sulfolane in the presence of tosyl acid. In addition to NaBH₃CN, other commercially available reducing agents such as NaBH₄, hydrazine (NH₂NH₂) with KOH or t-Buok and Zn with NH₃ in an aprotic polar solvent, e.g., dioxane, diethylene glycol, dimethylsulfoxide, alcohol, tetrahydrofuran and the like may also be used.

In Scheme (b), a cyclopentanone derivative II is reduced by LiAlH₄, NaBH₄, LiBH₄, NaAlH₂(CH₃OCH₂CH₂OCH₃)₂ under a controlled manner to a cyclopentanol derivative IIa followed by appropriate modifications to a compound of Formula Ia. One of such modifications is alkylation with a reagent of Formula R²X wherein X is halo, tosyl or mesyl in an aprotic solvent (e.g., DMSO, HMPA, THF, CH₃OCH₂CH₂OCH₃, xylene and toluene) and at about 25° to 150° C. in the presence of a base such as Na⁺DMSO⁻, NaNH₂, NaH, Ag₂O, n-BuLi and KN[Si(CH₃)₃]₂.

According to Scheme (c), the cyclopentanone derivative IIa may also be converted directly via appropriate conversions, for example, acetylation as described below in Scheme (d) and amination as described in Scheme (e).

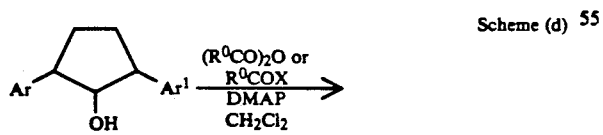

Scheme (d)

wherein X is halo;
R⁰ is C₁₋₆alkyl; and
DMAP is 4-dimethylaminopyridine

The conversion of one cyclopentane derivative to the other can be illustrated by the following examples:

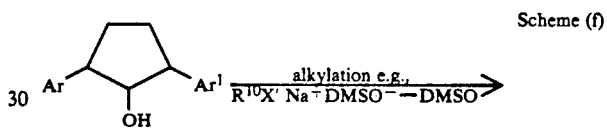

Scheme (f)

wherein R¹⁰ is R²; —CH₂COOR*; —CH₂—C≡CH; —CH₂C≡N; —CH₂CH=CH₂; —CH₂-phenyl or —CH₂-substituted phenyl as previously defined; —(CH₂)₂OC₁₋₆alkyl; —(CH₂)₂NR²₂; or —CH₂CONR²R³.

Scheme (g)

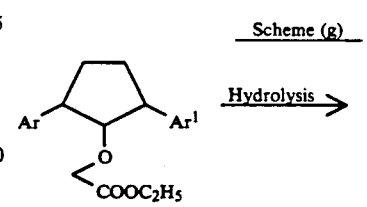

Hydrolysis →

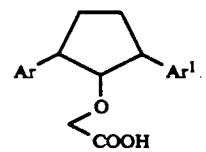

OR

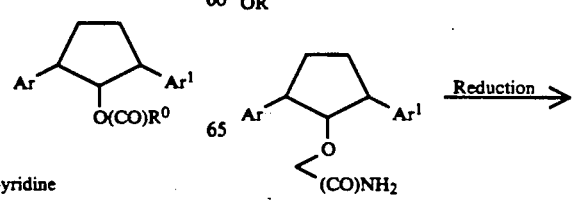

Reduction →

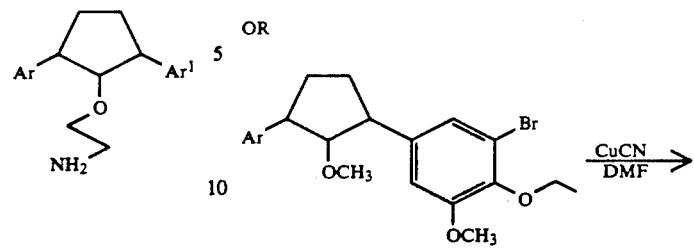
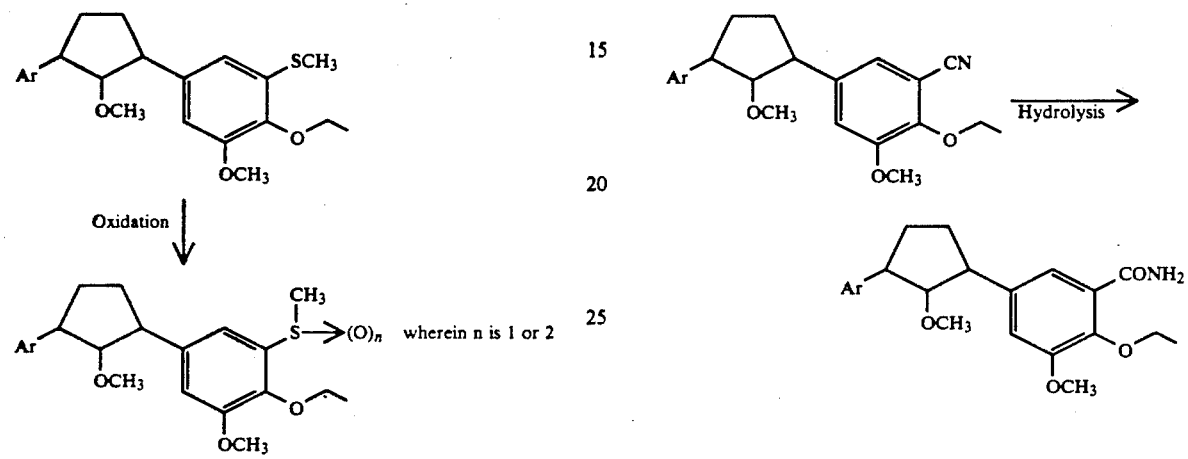
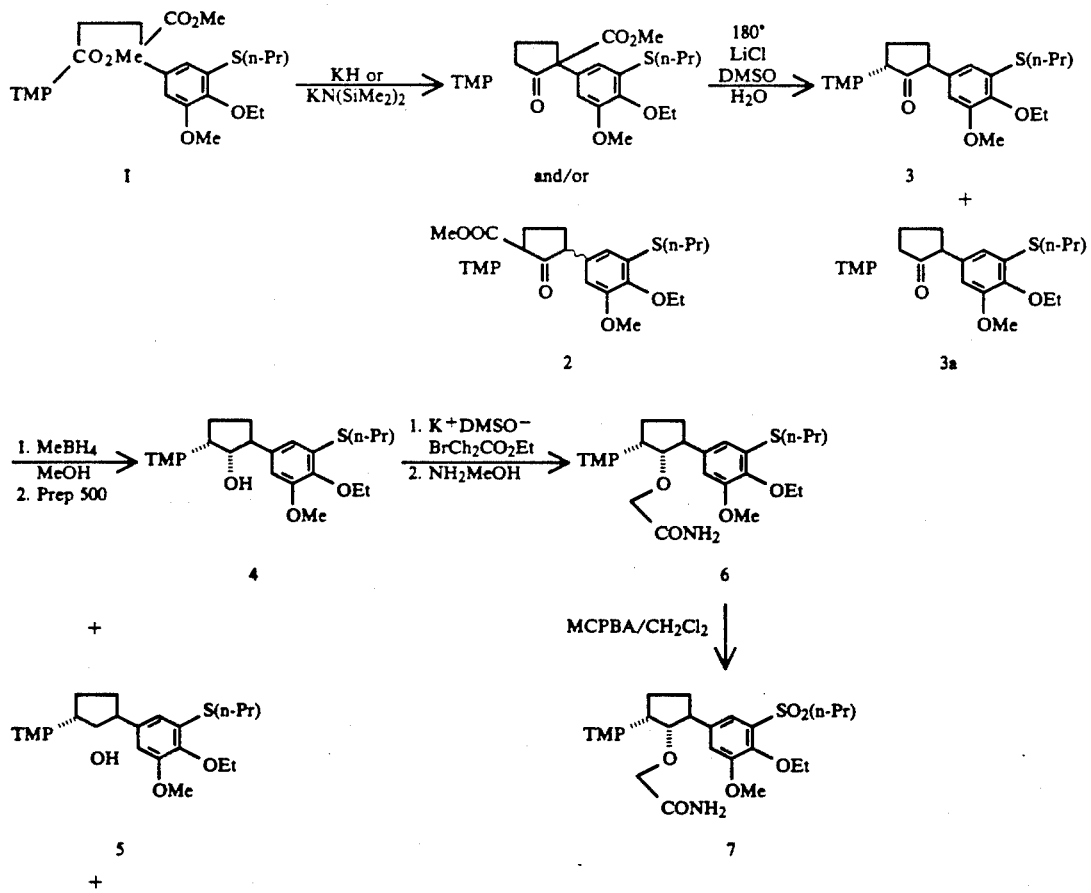

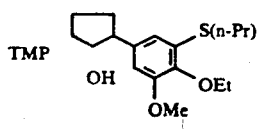

5a

Alternatively, the cyclopentanone starting material (II) can be prepared readily according to the following procedures, for example:

Method A: Preparation of Symmetrical Cyclopentanone Derivatives:

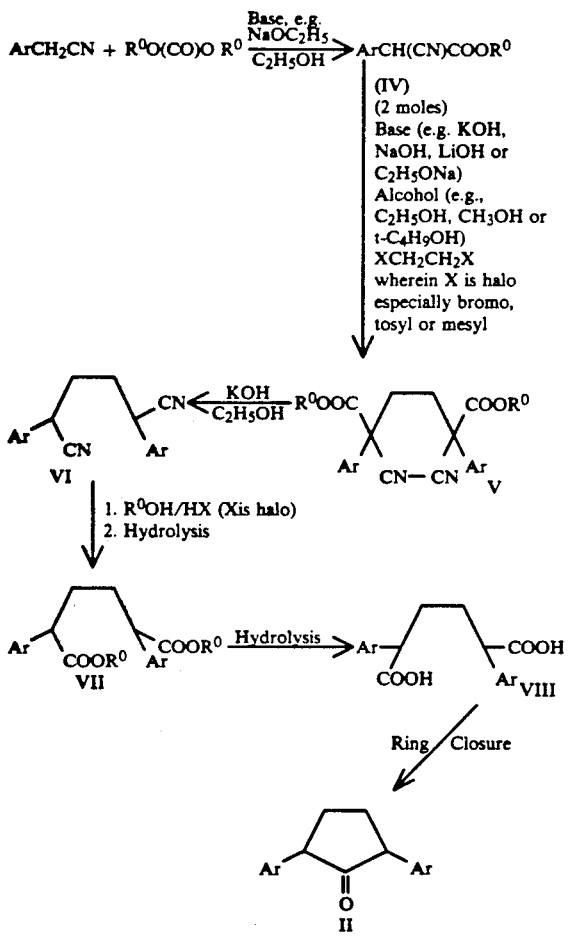

The formation of Compound IV and Compound V can also be effected by other commonly available bases, for example, $KOC_2H_5$, $NaOCH_3$, NaH, KH, $NaNH_2$ and t-Buok. Various solvent systems may be used, for example, xylene, benzene, $(C_2H_5)_2O$, DMF, DMSO, $CH_3O$ $CH_2CH_2OCH_3$, THF or an alcohol such as methanol or ethanol. The reaction is normally conducted under mild temperature from about 0° C. to about 150° C., preferably, from 25° C. to 100° C.

The conversion of Compound V to VI can be affected by a strong base including KOH, LiOH and NaOH. The reaction is normally carried out at about 0° C. to about 150° C. preferably 25° C.-100° C. in a protic solvent such as methanol and ethanol.

The conversion of Compound VI to VII can be effected by a strong acid such as HCl, HBr, HI, TsOH, $H_2SO_4$ or $H_3PO_4$ in an alcohol such as ethanol or methanol at about 20° C.-100° C. preferably 0° C.-40° C. followed by hydrolysis to VII. Compound VII in turn can be hydrolyzed to Compound VIII under conventional procedures. The catalysts for the hydrolysis can be acidic such as HCl, HBr and the like or basic such as KOH, NaOH or LiOH.

In order to facilitate ring closure of VIII which is normally conducted for about 2-10 minutes, preferably less than 5 minutes at high temperatures up to 290° C., preferably no higher than 270° C. in the presence of acetic anhydride or other dehydrating agent, e.g., $CH_3COX$, $C_2H_5O(CO)X$, DCC, and $(CF_3CO)_2O$. Alternatively the diacid VII can be converted to heavy metal salts such as those of Fe, Pb, Cd and Tl or alkaline earth metal salts such as those of Ba and Ca which in turn are pyrolyzed to give the symmetric cyclopentanones of Formula II.

Method B: Synthesis of Asymmetric Cyclopentanone Derivatives

As exemplified by Example 2, the synthesis of an asymmetric cyclopentanone involves the preparation of $ArC(CN)(COOR°)CH_2CH_2Br$ (VII) and $Ar^1CH(CN)COOR°$ according to the following scheme:

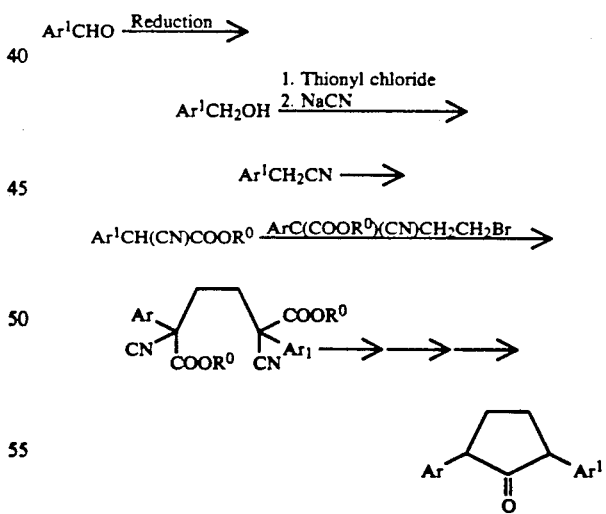

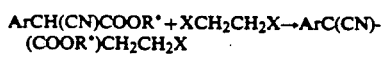

wherein Ar and $Ar^1$ are not identical.

The preparation of $ArC(CN)(COOR°)CH_2CH_2X$ requires the reaction between $ArCH(CN)COOR°$ and an excess amount of $XCH_2CH_2X$ wherein X is halo preferably Br:

$ArCH(CN)COOR° + XCH_2CH_2X \rightarrow ArC(CN)(COOR°)CH_2CH_2X$

The following examples illustrate how to prepare the compounds of the present invention.

EXAMPLE 1

1α-Methoxy-2α,5β-bis-(3,4,5-trimethoxyphenyl)cyclopentane and ether analogs

Step A: Preparation of α,α'-bis(3,4,5-Trimethoxyphenyl)adiponitrile

Most of the ethanol was removed by distillation at reduced pressure (bath <90° C.) from a solution of 17.3 g (0.752 g-atom) of sodium in ethanol (377 ml). 3,4,5-Trimethoxyphenylacetonitrile (150 g, 0.725 moles), diethyl carbonate (430 ml), and toluene (300 ml) were added, and the mixture heated under reflux in a nitrogen atmosphere with stirring. Ethanol was distilled while toluene was added at the same rate from a dropping funnel. When the distillation temperature reached 110°, the slurry was cooled and filtered. The yellow solid was washed with toluene and ether, dried briefly in a vacuum oven and suspended in ethanol (315 ml) and 1,2-dibromoethane (27.1 ml, 0.315 mole). The slurry was heated under reflux in a nitrogen atmosphere with stirring for 7 hours. After standing for 7 hours at room temperature the reaction mixture was transferred using 200 ml of ethanol into a solution of potassium hydroxide (61.9 g, 85.6%, 0.945 moles) in 2000 ml of ethanol. The suspension was heated at 50°-70° C. with stirring for 1.5 hours. After cooling the brown solid was filtered, washed with water (four times) and dried to give 76.8 g (48%) of α,α'-bis-(3,4,5-trimethoxyphenyl)adiponitrile, m.p. 173°-174.5°.

Step B: Preparation of Dimethyl α,α'-bis(3,4,5-trimethoxyphenyl)adipate

α,α'-bis(3,4,5-Trimethoxyphenyl)adiponitrile (11 g, 25 mmoles) was suspended in methanol (100 ml) and a vigorous stream of hydrogen chloride gas was passed into the slurry for 30 minutes while the temperature was kept below 30° C. with an ice bath. The pale yellow slurry was stirred at room temperature for 5.5 hours during which time the dinitrile slowly dissolves, then the iminoester hydrochloride precipitates suddenly. Ether (100 ml) was added and the solid quickly filtered, washed with ether and sucked dry briefly. The damp solid was immediately dissolved in water (100 ml). After a few minutes a solid precipitated. After stirring for 19 hours at room temperature the colorless solid was filtered, washed with water (three times) and dried to give 11.0 g (87%) of dimethyl α,α'-bis(3,4,5-trimethoxyphenyl)adipate, m.p. 179°-183.5°.

Step C: Preparation of α,α'-bis(3,4,5-trimethoxyphenyl)adipic acid

A mixture of dimethyl α,α'-bis(3,4,5-trimethoxyphenyl)adipate (11.0 g, 21.7 mmoles), potassium hydroxide (13.0 g, 202 mmoles), water (163 ml), and ethanol (65 ml) was heated at 90° in a nitrogen atmosphere for 3 hours. After cooling the clear solution was added slowly to 250 ml of 1N hydrochloric acid with vigorous stirring. The slurry was stirred and warmed to 50° for several minutes. After cooling in an ice bath the solid was filtered, washed with water (4 times) and dried to give 10.07 g (97%) of α,α'-bis(3,4,5-trimethoxyphenyl)adipic acid, m.p. 226°-223°. NMR (DMSO-$d_6$) indicates a 9:1 mixture of meso and racemic isomers.

Step D: Preparation of trans-2,5-bis(3,4,5-Trimethoxyphenyl)cyclopentanone

A mixture of α,α'-bis(3,4,5-trimethoxyphenyl)adipic acid (10 g, 21 mmoles) and acetic anhydride (30 ml) was heated at 150° C. for 30 minutes. Acetic acid and anhydride were removed in vacuo. The flask containing the solid residue was fitted with a distillation head and while under vacuum (~150 mm) was placed in an oil bath heated to 287° C. The solid melted; there was a vigorous evolution of gas and about 5 ml of liquid distilled. After 6.5 minutes the flask was cooled rapidly with a water bath. The yellow-brown syrupy residue was dissolved in 80 ml of hot ethanol, filtered from some insoluble material and seeded. After standing at room temperature overnight, the crystalline solid was filtered, washed with cold ethanol (3 times) and dried to give 5.57 g (64%) of trans-2,5-bis(3,4,5-trimethoxyphenyl)cyclopentanone, m.p. 140°-142.5°. IR 1740 cm$^{-1}$ (C=O), mass spec m/e 416 (M+).

Step E: Preparation of Trans-2,5-bis(3,4,5-trimethoxyphenyl)cyclopentanol

To a suspension of 2,5-bis(3,4,5-trimethoxyphenyl)cyclopentanone (1.16 g, 2.79 mmoles) in THF (15 ml) in a nitrogen atmosphere and cooled in an ice bath was added all at once lithium aluminum hydride (0.106 g, 2.79 mmoles). The cooling bath was removed, and the suspension stirred at room temperature for 3 hours. The mixture was cooled in an ice bath, and $H_2O$ (106 μl) was added cautiously followed by addition of 106 μl of 15% NaOH and 318 μl of $H_2O$. The suspension was stirred at room temperature for 30 minutes. $CH_2Cl_2$ (20 ml) was added, and the solid filtered and washed with $CH_2Cl_2$ (three times). The combined filtrate and washes were evaporated in vacuo. The syrupy residue (1.18 g) was crystallized from $CH_2Cl_2$-hexane to give 1.06 g (91%) of trans-2,5-bis(3,4,5-trimethoxyphenyl)cyclopentanol, m.p. 126°-128°.

Step F: Preparation of 1α-Methoxy-2α,5β-bis(3,4,5-trimethoxyphenyl)cyclopentane To a solution of trans-2,5-bis(3,4,5-trimethoxyphenyl)cyclopentanol (125 mg, 0.3 mmole) in DMSO (1 ml) was added at room temperature in an $N_2$ atmosphere a solution of $NaCH_2SOCH_3$ (2.0 M, 0.25 ml, 0.5 mmoles) in DMSO. After stirring for 10 minutes, MeI (38 μl, 0.6 mmoles) was added. After 20 minutes the reaction was diluted with $H_2O$ (15 ml) and extracted with $Et_2O$ (3 times). The combined ether extracts were washed with $H_2O$ (3 times) and saturated brine and dried ($MgSO_4$). The ether was removed in vacuo to give 129 mg of a colorless syrup. A 50 mg sample was crystallized from hexane to give 25 mg of 1α-methoxy-2α,5β-Bis-(3,4,5-trimethoxyphenyl) cyclopentane, m.p. 76°-78.5°. NMR (CDCl$_3$) β 6.56, 6.52 (s, 2H each, ArH), 3.82-3.92 (ms, 18H, ArOCH$_3$), 3.74 (m, 1H, CHOCH$_3$), 3.09 (s, 3H, CHCH$_3$).

Using the same procedure the following -2α,5β-Bis-(3,4,5-trimethoxyphenyl) ether compounds were prepared (non-crystalline compounds were purified by preparative TLC on silica gel with hexane:ethyl acetate in varying ratios):

| | | Scheme (f): | |
|---|---|---|---|
| R | X' | m.p. | NMR (CDCl₃, δ (ppm)) |
| CH₂C≡CH | Br | oil | 6.58, 6.56(s, 2H each, ArH), 4.06(m, 2H, OCH₂), 3.82-3.90 (ms, 18H, ArOCH₃), 3.74(m, 1H, CHOCH₂), 2.30(t, 1H, C≡CH). |
| CH₂CO₂Et | Br | oil | 6.57, 6.61(s, 2H each, ArH), 4.05(q, 2H, OCH₂CH₃), 3.82-3.92(ms, 19H, ArOCH3 + CHOCH₂), 3.62(s, 2H, OCH₂CO), 1.15(t, 3H, OCH₂CH₃). |
| CH₂CH=CH₂ | Br | oil | 6.58, 6.52(s, 2H each, ArH), 5.65, 5.06, 4.97(m, 1H each, CH=CH₂), 3.82-3.90(ms, 18H, ArOCH₃), 3.70(m, 1H, CHOCH₂), 3.62(m, 2H, CH₂CH=CH₂). |
| CH₂ | Br | oil | 6.52, 6.58(s, 2H each ArH) 3.82-3.90(ms, 18H, ArOCH₃), 3.78(m 1H, CHOCH₂), 2.6-3.2 (12 peak multiplet (restricted rotation), 2H, OCH₂—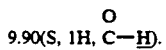), 0.88, 0.34, −.09(m, 5H, ◁). |
| CH₂CH₃ | I | oil | 6.53, 6.59(s, 2H each, ArH), 3.82-3.90(ms, 18H, ArOCH₃), 3.78(m, 1H, CHOCH₂), 2.9-3.35 (m, 4H, ArCH + OCH₂CH₃), 0.97 (t, 3H, OCH₂CH₃). |
| CH₂CH₂CH₃ | I | oil | 6.53, 6.57(s, 2H each, ArH), 3.82-3.90(ms, 18H, ArOCH₃), 3.76(m, 1H, CHOCH₂), 2.86-3.30(m, 4H, ArCH + OCH₂CH₂), 1.37(m, 2H, OCH₂CH₂CH₃), 0.72 (t, 3H, CH₂CH₃). |
| CH₂Ph | Br | oil | 7.18, 6.97(m, 5H, Ph), 6.48, 6.57(s, 2H each, ArH), 4.18 (q (restricted rotation), 2H, CH₂Ph), 3.76-3.92(ms, 19H, ArOCH₃ + CHOCH₂). |
| CH₂CH₂OCH₃ | Cl | oil | 6.59, 6.57(s, 2H each, ArH), 3.78-3.96(ms, 19H, ArOCH₃ + CHOCH₂), 3.05-3.40(m, 6H, ArCH + OCH₂CH₂O), 3.20 (s, 3H, CH₂OCH₃). |
| CH₂CN(CH₃)₂ (with C=O) | Cl | 112-114° | 6.57, 6.56(s, 2H each, ArH), 3.74-3.98(ms, 21H, ArOCH₃ + OCH₂CO + CHOCH₂), 2.77, 2.48(s, 3H each, N(CH₃)₂). |

EXAMPLE 2

2-(3-Methoxy-5-(methylthio)-4-propoxyphenyl)-5-(3,4,5-trimethoxyphenyl)cyclopentanone and 2-(3-bromo-5-methoxy-4-propoxyphenyl)-5-(3,4,5-trimethoxyphenyl)-cyclopentanone

Step A: Preparation of 3-bromo-5-methoxy-4-propoxybenzaldehyde 50 g (0.43 mole) of 5-bromovanillin in 130 ml of DMF was added 150 g (1.08 mole) of potassium carbonate and 55 ml (0.606 mole) of bromopropane. The mixture was stirred for 72 hours at 70° C. The solution was then poured into 1 liter ice water. The aqueous solution was extracted with 3×200 ml CH₂Cl₂, the combined organic extracts were dried over MgSO₄. The solution was filtered and the filtrate was concentrated to dryness to yield 66.80 g of 3-bromo-5-methoxy-4-propoxybenzaldehyde as a yellow oil. (95% yield).

NMR (CDCl₃): δ 1.03 (t, 3H, term. CH₃), 1.83 (m, 2H, OCH₂CH₂CH₃), 3.90 (s, 3H, OCH₃), 4.08 (t, 2H, OCH₂CH₂CH₃),

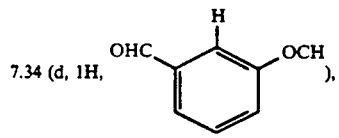

7.34 (d, 1H, ...)

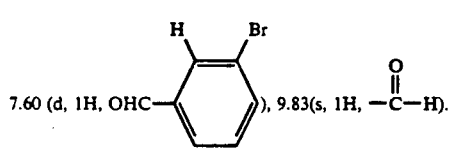

7.60 (d, 1H, OHC—...), 9.83(s, 1H, —C(=O)—H).

Step B: Preparation of 3-methoxy-5-methylthio-4-propoxybenzyl alcohol 50 (0.56 mole) of methyl disulfide in 400 ml of 2,4-lutidine was added 46 g (0.72 mole) of copper. The mixture was heated at 140° for 3 hours. The solution was cooled to room temperature and 74.90 g (0.56 mole) of 3-bromo-5-methoxy-4-propoxybenzaldehyde was then added. The mixture was refluxed for 16 hours at 175° C. The solution was filtered and the filtrate was concentrated to dryness. The product was purified by flash column chromatography first then recrystallized from hexane to give 17.01 g (26% yield) of 3-methoxy-5-methylthio-4-propoxybenzaldehyde as a white solid. m.p. 64°-66° C. NMR (CDCl₃): δ 1.1 (t, 3H, term CH₃), 1.79 (m, 2H, OCH₂CH₂CH₃), 2.47 (s, 3H, SCH₃), 3.87 (s, 3H, OCH₃), 4.05 (t, 2H, OCH₂CH₂CH₃), 7.20 (S, 2H, Ar-e,uns/H/ ), 9.90(S, 1H, C(=O)—H).

15.5 g (0.065 mole) of 3-methoxy-5-methylthio-4-propoxybenzaldehyde in 300 ml of methanol was cooled in ice bath. 1 g (0.026 mole) of sodium borohydride was added in 3 portions to the above solution. The mixture was stirred for 10 minutes in ice bath. MeOH was removed, and the residue was purified by flash column chromatography to afford 15.45 g (95% yield) of 3-methoxy-5-methylthio-4-propoxybenzyl alcohol as a light yellow oil.

NMR (CDCl₃): δ 1.06 (t, 3H, term 3H), 1.90 (m, 2H, —OCH₂CH₂CH₃), 2.43 (s, 3H, SCH₃), 3.86 (s, 3H, OCH₃), 3.97 (t, 2H, OCH₂CH₂CH₃), 4.63 (d, 2H, ArCH₂OH), 6.74 (s, 2H, Ar—H).

Similarly, starting with 3-bromo-5-methoxy-4-propoxybenzaldehyde and following only the sodium borohydride procedure of Step B, 3-bromo-5-methoxy-4-propoxybenzyl alcohol was prepared as a yellow oil in a 95% yield:

NMR (CDCl₃): δ 1.05 (m, 3H —OCH₂CH₂CH₃), 4.55 (s, 2H, Ar—CH₂—OH), 6.80 (d, 1H, Ar—H), 7.05 (d, 1H, Ar—H).

Step C: Preparation of 3-methoxy-5-methylthio-4-propoxyphenylacetonitrile 15.45 g (0.064 mole) of 3-methoxy-5-methylthio-4-propoxybenzyl alcohol was cooled in ice bath and 4.9 ml (0.065 mole) of thionyl chloride was added. The mixture was stirred for 30 minutes in ice bath. Solvent and the excess thionyl chloride were removed under vacuum. Because the product 3-methoxy-5-methylthio-4-propoxybenzyl chloride was a heat sensitive compound, the residue (16 g) was used in the next step without further purification.

To 16 g of 3-methoxy-5-methylthio-4-propoxybenzyl chloride in 100 ml of dry DMF was added 5 g (0.10 mole) sodium cyanide. The mixture was stirred for about 48 hours at rom temperature under $N_2$. The solution was filtered, and the filtrate was concentrated under vacuum. The residue was purified by flash column chromatography to yield 14.5 g of 3-methoxy-5-methylthio-4-propoxyphenyl acetonitrile as an oil. (95% yield).

NMR (CDCl$_3$): δ 3.65 (s, 2H, C$\underline{H}_2$CN), 1.04 (t, 3H, term C$\underline{H}_3$), 1.80 (m, 2H, OCH$_2$C$\underline{H}_2$CH$_3$), 2.40 (s, 3H, SC$\underline{H}_3$), 3.85 (s, 3H, OC$\underline{H}_3$), 3.95 (t, 2H, OC$\underline{H}_2$CH$_2$CH$_3$), 6.66 (s, 2H, Ar—$\underline{H}$).

Similarly, following the procedure of Step C, but substituted 3-bromo-5-methoxy-4-propoxyphenylbenzyl alcohol for 3-methoxy-5-methylthio)-4-propoxybenzyl alcohol, afforded 3-bromo-5-methoxy-4-propoxyphenylacetonitrile as a yellow oil in a 95% yield.

NMR (CDCl$_3$): δ 1.06 (m, 3H, —OCH$_2$CH$_2$C$\underline{H}_3$), 3.65 (s, 2H, —C$\underline{H}_2$—CN), 6.78 (d, 1H, Ar—H), 7.05 (d, 1H, Ar—H).

Step D: Preparation of Ethyl 3-Methoxy-5-methylthio-4-propoxy-α-cyanobenzeneacetate (V)

1.4 g of sodium was dissolved in absolute EtOH with warming to 70° C., then EtOH was removed under vacuum to give a white solid residue of NaOEt. A mixture of 35 ml of diethyl carbonate, 43 ml of toluene, 13.46 g of 3-methoxy-5-methylthio-4-propoxyphenyl acetonitrile was added slowly. The mixture was refluxed for 3 hours. EtOH was removed under vacuum. The solid was filtered and washed with toluene (3×) and ether (3×). The solid was suspended in 200 ml of H$_2$O and acidified with 6N HCl. The solid dissolved and a brown oil formed. The oil was extracted with ether (3×), the combined ether extracts were washed with H$_2$O (2×), saturated NaCl (2×) was finally dried over MgSO$_4$. The ether was removed under vacuum to give 16 g (92% yield) of ethyl 3-methoxy-5-methylthio-4-propoxy-α-cyanobenzeneacetate.

NMR (CDCl$_3$): δ 4.75 (s, 1H,

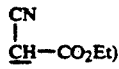

1.23 (m, 6H, COOCH$_2$C$\underline{H}_3$, OCH$_2$CH$_2$C$\underline{H}_3$), 1.80 (m, 2H, OC$\underline{H}_2$CH$_2$CH$_3$), 2.43 (s, 3H, SC$\underline{H}_3$), 3.83 (s, 3H, OC$\underline{H}_3$), 4.2 (m, 4H, OC$\underline{H}_2$CH$_2$CH$_3$,

6.73 (s, 2H, Ar—$\underline{H}$).

Similarly, following the procedure of Step D, but substituting 3-bromo-5-methoxy-4-propoxyphenylacetonitrile obtained in Step C for 3-methoxy-5-(methylthio)-4-propoxyphenylacetonitrile afforded ethyl 3-bromo-5-methoxy-4-propoxy-α-cyanobenzeneacetate as a yellow oil in a 60% yield.

NMR (CDCl$_3$); δ 1.05 (t, 3H, —OCH$_2$CH$_2$C$\underline{H}_3$), 1.28 (t, 3H —CO$_2$CH$_2$C$\underline{H}_3$), 3.88 (s, 3H, Ar—OC$\underline{H}_3$), 3.95 (t, 2H, —OC$\underline{H}_2$CH$_2$C$\underline{H}_3$), 4.24 (m, 2H), —CO$_2$C$\underline{H}_2$CH$_3$), 4.60 (s, 1H, —C$\underline{H}$(CN)CO$_2$Et), 6.90 (d, 1H, Ar—H), 7.18 (d, 1H, Ar—$\underline{H}$).

Following procedures similar to that of Step D but substituting 3,4,5-trimethoxyphenylacetonitrile for 3-methoxy-5-(methylthio)-4-propoxyphenylacetonitrile, there was prepared ethyl 3,4,5-trimethoxy-α-cyanobenzeneacetate in 89% yield as a clear oil.

NMR (CDCl$_3$): δ 1.35 (t, 3H, —CO$_2$CH$_2$C$\underline{H}_3$), 4.25 (q, 2H, —CO$_2$C$\underline{H}_2$CH$_3$), 4.65 (s, 1H, —C$\underline{H}$(CN)CO$_2$Et), 6.05 (s, 2H, Ar—$\underline{H}$).

Step E: Preparation of Ethyl 3,4,5-trimethoxy-α-(2-bromoethyl)-α-cyanobenzeneacetate To dry ethanol (100 ml) under a nitrogen atmosphere was added sodium (4.2 gm, 0.18 mol). After the sodium had completely dissolved, ethyl 3,4,5-trimethoxy-α-cyanobenzeneacetate (50.0 g, 0.18 mol) in ethanol (70 ml) was added dropwise over 30 minutes. A slight exotherm was observed. The reaction was heated to 90° C. for 30 minutes, then added dropwise over 2 hours to a refluxing solution of dibromoethane (340.0 g, 1.8 mol) in ethanol (500 ml). The reaction was refluxed an additional 3 hours, then concentrated. The residue was taken up in water (300 ml) and extracted with ethyl acetate (2 ×500 ml). The combined organic layers were washed with brine (1×100 ml), dried (MgSO$_4$) and concentrated to a solid. The solid was washed with hexane (2×200 ml) then recrystallized from hexane to give ethyl 3,4,5-trimethoxy-α-(2-bromoethyl)-α-cyanobenzeneacetate in 65% yield as a white solid, m.p. 76°-77° C.

NMR (CDCl$_3$): δ 1.30 (t, 3H, —CO$_2$CH$_2$C$\underline{H}_3$), 4.25 (q, 2H, CO$_2$C$\underline{H}_2$CH$_3$), 4.62 (s, 1H, —C$\underline{H}$(CN)CO$_2$Et), 6.65 (s, 2H, Ar—H).

Following procedures similar to the procedure of Step E but substituting ethyl 3-bromo-5-methoxy-4-propoxy-α-cyanobenzeneacetate for ethyl 3,4,5-trimethoxy-α-cyanobenzene acetate, there was prepared ethyl 3-bromo-5-methoxy-4-propoxy-α-(α-bromoethyl)-α-cyanobenzeneacetate in a 92% yield as a light yellow oil.

NMR (CDCl$_3$): δ 1.04 (t, 3H, —OCH$_2$CH$_2$C$\underline{H}_3$), 1.28 (t, 3H, —CO$_2$CH$_2$C$\underline{H}_3$), 3.88 (s, 3H, Ar—OC$\underline{H}_3$), 3.96 (t, 2H, OC$\underline{H}_2$CH$_2$C$\underline{H}_3$), 6.48 (d, 1H, Ar—H), 7.28 (d, 1H, Ar—$\underline{H}$).

Step F: Preparation of Diethyl 2-(3-Methoxy-5-(methylthio)-4-propoxyphenyl)-2,5-dicyano-5-(3,4,5-trimethoxyphenyl)-1,6-hexanedioate To a slurry of sodium hydride (0.065 g, 0.027 mol) in dimethylformamide (50 mL) was added dropwise ethyl 3-methoxy-5-(methylthio)-4-propoxy-α-cyanobenzeneacetate (6.8 g, 0.021 mol) in dimethyl formamide (15 ml) over 40 minutes at room temperature under nitrogen. The reaction was heated to 90° C. for 10 minutes, then ethyl 3,4,5-trimethoxy-2-(2-bromoethyl)-α-cyanobenzeneacetate (8.16 g, 0.021 mol) in dimethylformamide (20 ml) was slowly added. The reaction was kept at 95° C. for four hours then cooled, filtered and concentrated. The crude oil was purified by flash column (30% ethyl acetate/hexane as eluant) to afford diethyl 2-(3-methoxy-5-(methylthio)-4-propoxyphenyl)-2,5-dicyano-5-(3,4,5-trimethoxyphenyl)-1,6-hexanedioate in 62% yield as a white solid (m.p. 131°-132.5° C.).

NMR (CDCl$_3$): δ 1.04 (t, 3H, term C$\underline{H}_3$), 1.26 (m,

1.82 (m, 2H, OCH$_2$CH$_2$CH$_3$), 2.20 (2H, m, —CH$_2$CH$_2$), 2.44 (m+s, SCH$_3$+—CH$_2$CH$_2$—), 3.86 (m, 12H, OCH$_3$), 3.96 (m, 2H, OCH$_2$CH$_2$CH$_3$), 4.26 (q, 4H,

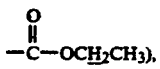

6.66, 6.74 (s, 2H, 2Ar—H), 6.75, 6.79 (d,d, 2H, ArH).

Following substantially the procedure of Step F but substituting ethyl 3,4,5-trimethoxy-α-cyanobenzeneacetate for ethyl 3-methoxy-5-(methylthio)-4-propoxy-α-cyanobenzeneacetate and substituting ethyl 3-bromo-5-methoxy-4-propoxy-α-(2-bromoethyl)-2-cyanobenzeneacetate for ethyl 3,4,5-trimethoxy-2-(2-bromoethyl)-α-cyano-benzeneacetate, there was prepared diethyl 2-(3-bromo-5-methoxy-4-propoxyphenyl)2,5-dicyano-5-(3,4,5-trimethoxyphenyl)-1,6-hexanedioate as an oil in a 63% yield. The product is a mixture of diastereoisomers.

NMR (CDCl$_3$): δ 1.25 (m, 3H, —OCH$_2$CH$_2$CH$_3$), 1.26 (m, 3H, —CO$_2$CH$_2$CH$_3$) 6.68 (s, Ar—H), 6.74 (s, Ar—H), 6.92 (d, Ar—H), 6.97 (d, Ar—H), 7.22 (d, Ar—H), 7.31 (d, Ar—H).

Step G: Preparation of 2-(3-methoxy-5-(methylthio)-4-propoxyphenyl)-5-(3,4,5-trimethoxyphenyl)-1,6-hexanedinitrile To a solution of diethyl 2-(3-methoxy-5-(methylthio)-4-propoxyphenyl)-2,5-dicyano-5-(3,4,5-trimethoxyphenyl)-1,6-hexanedioate (12.0 g, 0.019 mol) in ethanol (250 ml) was added potassium hydroxide (4.4 g, 0.079 mol). The reaction was heated to 95° C. for 20 minutes, then filtered, and the filtrate concentrated. Methanol (300 ml) was added to the residue, and the solution was stirred at room temperature overnight. The reaction was filtered and the precipitate dried to yield 2-(3-methoxy-5-methylthio)-4-propoxyphenyl)-5-(3,4,5-trimethoxyphenyl)-1,6-hexanedinitrile in a 66% yield. (m.p. 131°-132.5° C.). NMR (CDCl$_3$): δ 1.04 (t, 3H, term CH$_3$), 1.80 (m, 2H, OCH$_2$CH$_2$CH$_3$), 2.18 (m, 2H, CH$_2$from

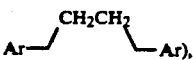

2.44 (m+s, SCH$_3$—CH$_2$from

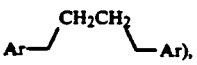

3.90 (m, 14H, —OCH$_3$+OCH$_2$CH$_2$CH$_3$), 6.64+6.72 (s, 2H, ArH), 6.71, 6.77, 6.81, 6.83 (d,d, 2H, ArH).

Following substantially the same procedure of Step G, but substituting diethyl 2-(3-bromo-5-methoxy-4-propoxyphenyl)-2,5-dicyano-5-(3,4,5-trimethoxyphenyl)-1,6-hexanedioate for diethyl 2-(3-methoxy-5-(methylthio)-4-propoxyphenyl)-2,5-dicyano-5-(3,4,5-trimethoxyphenyl)-1,6-hexanedioate there was obtained 2-(3-bromo-5-methoxy-4-propoxyphenyl)-(3,4,5-trimethoxyphenyl)-1,6-hexanedinitrile as an oil in 30% yield.

NMR (CDCl$_3$): δ 1.05 (t, 3H, —OCH$_2$CH$_2$CH$_3$), 1.82 (m, 2H —OCH$_2$CH$_2$CH$_3$), 3.95 (t, 2H, —OCH$_2$CH$_2$CH$_3$), 6.50 (s, 2H, Ar—H), 6.95 (d, 1H, Ar—H), 7.05 (d, 1H, Ar—H).

Step H: Preparation of 2-(3-methoxy-5-methylthio-4-propoxyphenyl)-5-(3,4,5-trimethoxyphenyl)-1,6-hexanedioic acid A solution of 2-(3-methoxy-5-(methylthio)-4-propoxyphenyl)-(3,4,5-trimethoxyphenyl)-1,6-hexanedinitrile (3.0 g, 0.0062 mol) in hydrochloric acid saturated methanol (240 ml) was stirred overnight at room temperature. The reaction was concentrated, and the residue taken up in water (200 ml) and stirred at room temperature for 40 hours. The resulting precipitate was filtered and washed with water then dissolved in water/ethanol 4:1 (150 ml) containing 3.4 g of potassium hydroxide. The solution was heated to 95° C. for 18 hours, cooled, filtered, and the filtrate neutralized with 37% hydrochloric acid. The resulting precipitate was washed with water and dried to yield 2-(3-methoxy-5-(methylthio)-4-propoxyphenyl)-5-(3,4,5-trimethoxyphenyl)-1,6-hexanedioic acid as a white solid (67%). m.p.=172°-173.5° C. NMR (CDCl$_3$): δ 1.03 (t, 3H, term CH$_3$), 1.8-2.0 (m, 6H, OCH$_2$CH$_2$CH$_3$,

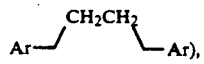

2.37 (s, 3H, SCH$_3$), 3.50 (m, 2H, ArCH—), 3.80 (m, 12H, OCH$_3$), 3.90 (2H, t, OCH$_2$CH$_2$CH$_3$), 6.48 (s, 2H, ArH), 6.61 (s, 2H, ArH).

Following substantially the same procedure of Step H but substituting 2-(3-bromo-5-methoxy-4-propoxyphenyl)-(3,4,5-trimethoxyphenyl)-1,6-hexanedinitrile for 2-(3-methoxy-5-(methylthio)-4-propoxyphenyl)-(3,4,5-trimethoxyphenyl)-1,6-hexanedinitrile there was obtained 2-(3-bromo-5-methoxy-6-propoxyphenyl)-5-(3,4,5-trimethoxyphenyl)-1,6-hexanedioic acid in a 69% yield as an oil.

NMR (CDCl$_3$): δ 1.03 (t, 3H, —OCH$_2$CH$_2$CH$_3$), 3.36-3.55 (m, 2H, (—CH(CO$_2$H)—), 6.48 (m, 2H, Ar—H), 6.72 (m, 1H, Ar—H), 7.05 (m, 1H, Ar—H).

Step I: Preparation of 2-(3-methoxy-5-(methylthio)-4-propoxyphenyl)-5-(3,4,5-trimethoxyphenyl)-cyclopentanone A solution of 2-(3-methoxy-5-(methylthio)-4-propoxyphenyl)-5-(3,4,5-trimethoxyphenyl)-1,6-hexanedioic acid (0.86 g, 1.6 mmol) and acetic anhydride (5 ml) was heated to 130°-135° C. for 30 minutes, then the excess solvent was removed. The pale yellow oil residue was then heated for 6 minutes at 275°-280 ° C., cooled, and purified by preparative TLC developed with 30% ethyl acetate-hexane to afford a 44% yield of 2-(3-methoxy-5-(methylthiol)-4-propoxyphenyl)-5-(3,4,5-trimethoxyphenyl)-cyclopentanone as a 1:4 cis:trans mixture.

Mass spectrum: m/e 460 (M+) NMR (CDCl$_3$): δ 1.40 (t, 3H, term, CH$_3$), 1.80 (m, 2H, OCH$_2$CH$_2$CH$_3$), 2.15 (m, 2H, cyclopentane CH$_2$), 2.41 (s, 3H, SCH$_3$), 2.61 (m, 2H, cyclopentane CH$_2$), 3.40-3.60 (broad m, 2H, ArCH), 3.76-3.96 (m, 14H, 4-OCH$_3$+OCH$_2$CH$_2$CH$_3$), 6.39, 6.54, 6.64 (s, 4H, Ar—H).

Following substantially the same procedure of Step I but substituting 2-(3-bromo-5-methoxy-6-propoxyphenyl)-5-(3,4,5-trimethoxyphenyl)-1,6-hexanedioic acid for 2-(3-methoxy-5-(methylthio)-4-propoxyphenyl)-5-(3,4,5-trimethoxyphenyl)-1,6-hexanedioic acid there was prepared a 1:4 cis:trans mixture of 2-(3- bromo-5-methoxy-4-propoxyphenyl-5-(3,4,5-trimethoxyphenyl)cyclopentanone as an oil in a 15% yield.

NMR (CDCl$_3$): δ trans isomer δ 1.06 (m, 3H, —OCH$_2$CH$_2$CH$_3$), 3.35-3.50 (m, 2H, cyclopentyl α-H), 6.47 (s, 2H, Ar—H), 6.80 (d, 1H, Ar—H), 7.00 (d, 1H, Ar—H).

cis isomer δ 1.06 (m, 3H, —OCH$_2$CH$_2$CH$_3$), 3.50-3.60 (m, 2H, cyclopentyl α-H), 6.32 (s, 2H, Ar—H), 6.70 (d, 1H, Ar—H), 7.00 (d, 1H, Ar—H).

EXAMPLE 3

2-(3-Methoxy-5-(methylthio)-4-propoxyphenyl)-5-(3,4,5-trimethoxyphenyl)cyclopentanol To a solution of 2-(3-methoxy-5-(methylthio)-4-propoxyphenyl)-5-(3,4,5-trimethoxyphenyl)cyclopentanone (0.40 g, 0.87 mmol) in methanol (20 ml) was added sodium borohydride (0.10 mg. 2.6 mmol). The reaction was refluxed for 30 minutes, then quenched into water (50 ml) and extracted with ether (3×50 ml). The combined organic extracts were washed with brine (50 ml), dried (MgSO$_4$) and concentrated to give a total yield of 55% of 2-(3-methoxy-5-(methylthiol)-4-propoxyphenyl)-5-(3,4,5-trimethoxyphenyl)cyclopentanol as a 1:2:2 mixture of the isomers A, B, and C (in order of increasing polarity). The isomers were separated by preparative TLC developed with 30% ethyl acetate-hexane.

Physical Data of the Isomers

A. 2α-(3-methoxy-5-methylthio-4-propoxyphenyl)-5=-(3, 4,5-trimethoxyphenyl)-1α-cyclopentanol
m.p.=94°-95.5° C.
mass spectrum: m/e 462 (M+).

B. 2β-(3-methoxy-5-methylthio-4-propoxyphenyl)-5α-(3,4,5-trimethoxyphenyl)-1β-cyclopentanol
m.p.=102.5°-104.5° C.
mass spectrum: m/e 462 (M+).
Analysis=C$_{25}$H$_{34}$O$_6$S. ½ H$_2$O (M.W.=467.1). Calc for: C, 64.28; H, 7.44. Found: C, 64.26; H, 7.43.

C. 2β-(3-methoxy-5-methylthio-4-propoxyphenyl)-5α-(3,4,5-trimethoxyphenyl)-1α-cyclopentanol
m.p.=98°-99° C.
mass spectrum: m/e 462 (M+).
Analysis=C$_{25}$H$_{34}$O$_6$S (M.W.=462.60). Calc for: C, 64.91; H, 7.41. Found: C, 65.31; H, 7.42.

EXAMPLE 4

2-(3-Bromo-5-methoxy-4-propoxyphenyl)-5-(3,4,5-trimethoxyphenyl)cyclopentanol

Following substantially the same procedure of Example 3, but substituting 2-(3-bromo-5-methoxy-4-propoxyphenyl)-5-(3,4,5-trimethoxyphenyl)cyclopentanone for 2-(3-methoxy-5-(methylthio)-4-propoxyphenyl)-5-(3,4,5-trimethoxyphenyl)cyclopentanone there was prepared 2-(3-bromo-5-methoxy-4-propoxyphenyl)-5-(3,4,5-trimethoxyphenyl)cyclopentanol in a 50% yield of a 1:2:2 mixture of isomers (1α, 2α, 5α):(1α, 2β, 5α):(1β, 2β,5α) in order of increasing polarity. The isomers were separated by preparative TLC developed with 30% ethyl acetate-hexane. NMR (CDCl$_3$):

isomer (1α, 2α, 5α): δ 1.06 (t, 3H, —OCH$_2$CH$_2$CH$_3$), 1.84 (m, 2H, —OCH$_2$CH$_2$CH$_3$), 3.20-3.40 (m, 2H, ArCH), 4.25-4.30 (m, 1H, cyclopentyl CHOH), 6.60 (s, 2H, Ar—H), 6.88 (d, 1H, Ar—H), 7.11 (d, 1H, Ar—H).

isomer (1α, 2α, 5α): δ 1.06 (t, 3H, —OCH$_2$CH$_2$CH$_3$), 1.84 (m, 2H, —OCH$_2$CH$_2$CH$_3$), 3.10-3.34 (m, 2H, ArCH), 4.12-4.14 (m, 1H, cyclopentyl CHOH), 6.52 (s, 2H, Ar—H), 6.75 (d, 1H, Ar—H), 7.08 (d, 1H, Ar—H).

isomer (1β, 2β, 5α): δ 1.06 (t, 3H, —OCH$_2$CH$_2$CH$_3$), 1.84 (m, 2H, —OCH$_2$CH$_2$CH$_3$), 3.08-3.34 (m, 2H, ArCH), 4.12-4.22 (m, 1H, cyclopentyl CHOH), 6.52 (s, 2H, Ar—H), 6.08 (d, 1H, Ar—H), 7.06 (d, 1H, Ar—H).

EXAMPLE 5

1α-Methoxy-2β-(3-methoxy-5-methylthio-4-propoxyphenyl)-5α(3,4,5-trimethoxyphenyl)cyclopentane Approximately 10 mg of sodium hydride in 1.5 ml of DMSO was heated at 75° C. for 40 minutes until the evolution of hydrogen ceased and the solution turned clear. To the above cooled sodium methylsulfinyl carbanion solution 30 mg of 2β-(3-methoxy-5-methylthio-4-propoxyphenyl)-5α-(2,3,4-trimethoxyphenyl)-1α,2α,-5α)cyclopentanol (isomer C) in 1 ml of DMSO was added slowly. The mixture was stirred for 20 minutes at room temperature until the color turned dark blue. Excess methyl iodide (500 μl) was added to the dark blue solution. The blue color disappeared immediately. The mixture was stirred for another 10 minutes at room temperature. The DMSO was removed and the residue was purified by preparation TLC (30% ethyl acetate-hexane) to yield 24 mg of 1α-methoxy-2β-(3-methoxy-5-methylthio-4-propoxyphenyl)-5α(3,4,5-trimethoxyphenyl)-cyclopentane. (73% yield)

Mass spectrum: m/e 476 (M+) NMR (CDCl$_3$): δ 3.09 (s, 3H, 1α-OCH$_3$).

Following essentially the same procedures as described above, there were prepared the following compounds:

(a) 1α-Methoxy-2α-(3-methoxy-5-methylthio-4-propoxyphenyl)-5α-(3,4,5-trimethoxyphenyl)cyclopentane (yield, 70%).
Mass spectrum: m/e 476 (M+)
NMR (CDCl$_3$): δ 2.81 (s, 3H, 1α-OCH$_3$).

(b) 1β-Methoxy-2β-(3-methoxy-5-methylthio-4-propoxyphenyl)-5α-(3,4,5-trimethoxyphenyl)cyclopentane (yield, 79%);
Mass spectrum: m/e 476 (M+)
NMR (CDCl$_3$): δ 3.08 (s, 3H, 1β-OCH$_3$).

(c) 1α-Methoxy-2β-(3-bromo-5-methoxy-4-propoxyphenyl)-5α-(3,4,5-trimethoxyphenyl)cyclopentane (yield, 56%);
NMR (CDCl$_3$): δ 3.08 (S, 3H, 1α-OCH$_3$).

(d) 1β-Methoxy-2β-(3-bromo-5-methoxy-4-propoxyphenyl)-5α-(3,4,5-trimethoxyphenyl)cyclopentane (yield 65%);
NMR (CDCl$_3$): δ 3.07 (s, 3H, 1β,—OCH$_3$).

EXAMPLE 6

1β-Methoxy-2β-(3-methoxy-5-methylsulfonyl-4-propoxyphenyl)-5α-(3,4,5-trimethoxyphenyl)cyclopentane and the corresponding sulfinyl derivative To a solution of 17 mg of 1β-methoxy-2β-(3-methoxy-5-methylthio-4-propoxyphenyl)-5α-(3,4,5-trimethoxyphenyl)cyclopentane in 2 ml of methylene chloride was added 80 mg of metachloroperoxybenzoic acid. The mixture was stirred at room temperature for about 30 minutes. The crude products were isolated and purified by preparative TLC (30% ethyl acetate-hexane) to yield the title compound in 58% yield; Mass spectrum: m/e 509 (M+); NMR (CDCl$_3$): δ 3.08 (s, 3H, 1β-OCH$_3$), 3.25 (s, 3H, SO$_2$CH$_3$) and the corresponding sulfinyl derivative in 19% yield, Mass spectrum: m/e 492 (M+), NMR (CDCl₃): δ 3.08 (s, 3H, 1β-OCH₃), 2.79 (d, 3H, SOCH₃).

Following essentially the same procedures as described above, the following compounds were prepared:

(a) 1α-Methoxy-2α-(3-methoxy-5-methylsulfonyl-4-propoxyphenyl)-5α-(3,4,5-trimethoxypheny)cyclopentane in 40% yield; Mass spectrum: m/e 509 (M+); NMR (CDCl₃): δ 2.76 (s, 3H, 1α-OCH₃), 3.24 (s, 3H, SO₂CH₃); m.p. 140.5°-142° C.

(b) 1α-Methoxy-2α-(3-methoxy-5-methylsulfinyl-4-propoxyphenyl)-5α-(3,4,5-trimethoxyphenyl)cyclopentane in 30% yield; Mass spectrum: m/e 492 (M+); NMR (CDCl₃): δ 2.78 (d, 3H, SOCH₃), 2.80 (s, 3H, 1α-OCH₃).

(c) 1α-Methoxy-2β-(3-methoxy-5-methylsulfonyl-4-propoxyphenyl)-5α-(3,4,5-trimethoxyphenyl)cyclopentane in 30% yield, Mass spectrum: m/e 509 (M+); NMR (CDCl₃): δ 3.05 (s, 3H, 1α-OCH₃), 3.28 (s, 3H, SO₂CH₃).

(d) 1α-Methoxy-2β-(3-methoxy-5-methylsulfinyl-4-propoxyphenyl)-5α-(3,4,5-trimethoxyphenyl)cyclopentane in 40% yield, Mass spectrum: m/e 492 (M+); NMR (CDCl₃): δ 3.07 (d, 3H, 1α-OCH₃), 2.83 (d, 3H, SOCH₃).

EXAMPLE 7

1β-Methoxy-2β-(5-cyano-3-methoxy-4-propoxyphenyl)-5α-(3,4,5-trimethoxyphenyl)cyclopentane To a solution of 1β-Methoxy-2β-(5-bromo-3-methoxy-4-propoxyphenyl)-5α-(3,4,5-trimethoxyphenyl)cyclopentane (22.0 mg, 0.043 mmol) in N-methylpyrrolidone (1.5 mL) was added cuprous cyanide (35.0 mg, 0.39 mmol). The reaction was heated to 175° C. for 8 hours, cooled, quenched into water (20 ml) and filtered. The filtrate was extracted with methylene chloride (3×25 ml). The combined organic layers were washed with brine (1×20 ml) dried (MgSO₄) and concentrated. The resulting brown oil was purified by preparative TLC developed with 30% ethyl acetatehexane. 1β-Methoxy-2β-(5-cyano-3-methoxy-4-propoxyphenyl)-5α-(3,4,5-trimethoxyphenyl)cyclopentane was obtained in a 51% yield as a clear oil.

NMR (CDCl₃): δ 1.06 (t, 3H, —OCH₂CH₂CH₃), 1.84 (m, 2H, —OCH₂CH₂CH₃), 3.08 (s, 3H, 1β—OCH₃), 3.68-3.78 (m, 1H, cyclopentyl CHOCH₃), 6.56 (s, 2H, Ar—H), 7.02-7.10 (m, 2H, Ar—H).

Following substantially the same procedures as described above there was prepared 1α-methoxy-2β-(5-cyano-3-methoxy-4-propoxyphenyl)-5α-(3,4,5-trimethoxyphenyl)cyclopentane in a 59% yield as a clear oil.

NMR (CDCl₃): δ 1.06 (t, 3H, —OCH₂CH₂CH₃), 1.84 (m, 2H, —OCH₂CH₂CH₃), 3.10 (s, 3H, 1α-OCH₃), 3.70-3.78 (m, 1H, cyclopentyl CHOCH₃), 6.30 (s, 2H, Ar—H), 7.04-7.12 (m, 2H, Ar—H).

EXAMPLE 8

1β-Methoxy-2β-(5-amido-3-methoxy-4-propoxyphenyl)-5α-(3,4,5-trimethoxyphenyl)cyclopentane A solution of 1β-methoxy-2β-(5-cyano-3-methoxy-4-propoxyphenyl)-5α-(3,4,5-trimethoxyphenyl)cyclopentane (7.0 mg, 0.015 mmol) in 10% sodium hydroxide in 3:1, ethanol:water (1.0 ml) was refluxed for 3½ hours. The reaction was cooled, then quenched into water (5 ml) and extracted with methylene chloride (3×5 ml). The combined organic layers were washed with brine (1×5 ml), dried (MgSO₄) and concentrated to a clear oil. The oil was purified by preparative TLC developed with 55% ethyl acetate hexane to afford a 56% yield of 1β-methoxy-2β-(5-amido-3-methoxy-4-propoxyphenyl)-5α-(3,4,5-trimethoxyphenyl)cyclopentane.

NMR (CDCl₃): δ 1.04 (t, 3H, —OCH₂CH₂CH₃), 3.08 (s, 3H, 1β—OCH₃), 4.04 (t, 2H, —OCH₂CH₂CH₃), 5.72 (m, 1H, —CONH₂), 6.57 (s, 2H, Ar—H), 7.00 (d, 1H, Ar—H), 7.65 (d, 1H, Ar—H), 7.99 (m, 1H, CONR₂).

Following essentially the same procedure as described above, there was prepared the following compounds: 1α-methoxy-2β-(5-amido-3-methoxy-4-propoxyphenyl)-5α-(3,4,5-trimethoxyphenyl)cyclopentane in a 41% yield as a clear oil.

NMR (CDCl₃): δ 1.06 (t, 3, —OCH₂CH₂CH₃), 3.08 (s, 3H, 1α-OCH₃), 4.04 (t, 2H, —OCH₂CH₂CH₃) 5.79 (m, 1H, CONH₂), 6.52 (s, 2H, Ar—H), 7.10 (d, 1H, Ar—H), 7.65 (d, 1H, Ar—H) 8.02 (m, 1H, CONH₂).

EXAMPLE 9

Trans-2,5-bis(3,4,5-trimethoxyphenyl)cyclopentanone-O-methyloxime

A mixture of trans-2,5-bis(3,4,5-trimethoxyphenyl)cyclopentanone (208 mg, 0.5 mmoles), NaOAc (82 mg, 1 mmole), CH₃ONH₂.HCl (83.5 mg, 0.5 mmole) and EtOH (1 ml) was heated at 90° in N₂atmosphere with stirring for 4 hours. After standing overnight at room temperature the mixture was diluted with H₂O (10 ml) and extracted with CH₂Cl₂ (three times). The combined CH₂Cl₂extracts were washed with H₂O and dried (MgSO₄). Evaporation of the CH₂Cl₂ in vacuo gave 223 mg of a colorless gum. Purification by preparative TLC (silica gel, hexane EtOAc, 1:1) gave 139 mg of trans-2,5-bis(3,4,5-trimethoxyphenyl)cyclopentanone-O-methyloxime, m.p. 61°-63°.

Using the same procedure trans-2,5-bis(3,4,5-trimethoxyphenyl)cyclopentanone oxime was prepared.

EXAMPLE 10

Trans-2,5-bis(3,4,5-trimethoxyphenyl)cyclopentanamine hydrochloride

To a solution of trans-2,5-bis(3,4,5-trimethoxyphenyl)cyclopentanone-O-methyloxime (53 mg, 0.12 mmoles) in THF (1 ml) cooled in an ice bath was added BH₃.THF (1M, 0.5 ml, 0.5 mmoles). The solution was heated in a N₂atmosphere at 55° for 20 hours. The clear solution was cooled in an ice bath and 3 ml of 10% NaOH was added. After dilution with H₂O (10 ml), the mixture was extracted with Et₂O (three times). The combined Et₂O extracts were shaken with 0.5 M HCl (three times). The combined acidic extracts were basified with 50% NaOH and extracted with Et₂O (three times). The combined Et₂O extracts were washed with H₂O and saturated brine and dried (K₂CO₃). Evaporation of the solvent in vacuo gave 19 mg of a colorless oil. This material was dissolved 10 ml of Et₂O and a stream of HCl gas was bubbled in for a few seconds. The Et₂O was evaporated in vacuo to give 20 mg of trans-2,5-bis(3,4,5-trimethoxyphenyl)cyclopentanamine hydrochloride, m.p. 270°-272° dec.

EXAMPLE 11

1α,3β-bis(3,4,5-trimethoxyphenyl)cyclopentane

Step A: Preparation of trans-2,5-bis(3,4,5-trimethoxyphenyl)cyclopentanone-p-toluenesulfonylhydrazone A mixture of trans-2,5-bis(3,4,5-trimethoxyphenyl)-cyclopentanone (97 mg, 0.23 mmoles) and EtOH (1.0 ml) was heated under reflux in a $N_2$ atmosphere for 5 hours. The cooled reaction mixture was filtered, and the solid washed with cold EtOH (two times) and dried to give 85 mg of trans-2,5-bis(3,4,5-trimethoxyphenyl)cyclopentanone p-toluenesulfonylhydrazone.

Step B: Preparation of 1α,3β-bis(3,4,5-trimethoxyphenyl)cyclopentane

A mixture of trans-2,5-bis(3,4,5-trimethoxyphenyl)-cyclopentanone p-toluenesulfonylhydrazone (80 mg, 0.137 mmoles), $NaBH_3CN$ (35 mg, 0.548 mmoles), p-toluenesulfonic acid (7 mg), DMF (0.34 ml) and sulfolane (0.34 ml) was heated at 110° in an $N_2$ atmosphere with stirring for 2 hours. Over the next two days the same amounts of $NaBH_3CN$ and p-toluenesulfonic acid were added followed by heating for 2-3 hours a total of five more times. The reaction mixture was diluted with $H_2O$ (15 ml) and extracted with $CH_2Cl_2$ (four times). The $CH_2Cl_2$ extracts were washed with $H_2O$ (three times) and dried ($MgSO_4$). Evaporation of the solvent in vacuo gave 62 mg of a brown oil. Purification by preparative TLC (silica gel, hexane-EtOAc, 1:1) gave 13 mg of 1α,3β-bis(3,4,5-trimethoxyphenyl)cyclopentane as a colorless oil; mass spectrum: m/e 402 (M+).

EXAMPLE 12

1α-acetoxy-2α,5β-bis(3,4,5-trimethoxypheny)cyclopentane

To a solution of trans-2,5-bis(3,4,5-trimethoxyphenyl)cyclopentanol (41.8 mg, 0.1 mmole), 4-dimethylaminopyridine (12 mg, 0.1 mmole) in $CH_2Cl_2$ (0.2 ml) was added acetic anhydride (19 μl, 0.2 mmole). The mixture was allowed to stand at room temperature for 20 hours. It was diluted with EtOAc and purified by preparative TLC (silica gel, hexane-EtOAc, 1:1) to give 1α-acetoxy-2α,5β-bis(3,4,5-trimethoxyphenyl)cyclopentane as a colorless syrup.

NMR ($CDCl_3$): δ 6.58, 6.51 (s, 2H each, ArH), 5.36 (m, 1H, C$\underline{H}$OAc), 3.80-3.90 (ms, 18H, ArOCH_3), 2.20 (s, 3H,

OCCH_3).

EXAMPLE 13

1α-(2α,5β-bis(3,4,5-Trimethoxyphenyl)cyclopentyl)oxy)acetic acid

A mixture of ethyl 1α-((2α,5β-bis-(3,4,5-trimethoxyphenyl)cyclopentyl)oxy)acetate (20 mg); MeOH (5 ml), and 50% NaOH (0.1 ml) was stirred at room temperature in a $N_2$ atmosphere for 4 hours. Most of the MeOH was removed on a rotary evaporator (bath 50°). The clear solution was diluted with $H_2O$ (10 ml), extracted with $Et_2O$, and acidified with concentrated HCl. The cloudy solution was extracted with $Et_2O$ (3 times). The combined $Et_2O$ extracts were washed with $H_2O$ and saturated brine and dried ($MgSO_4$). Removal of the solvent in vacuo gave 13 mg of 1α-((2α,5β-bis(3,4,5-trimethoxyphenyl)cyclopentyl)oxy)acetic acid as a colorless syrup.

NMR ($CDCl_3$): δ 6.53, 6.48 (s, 2H each, ArH), 3.82-3.90 (mg, 19H, ArOCH_3+C$\underline{H}$OCH_2), 3.78 (q, restricted rotation, 2H, OCH_2CO).

EXAMPLE 14

1α-N,N-dimethylaminoethoxy-2α,5β-bis(trimethoxyphenyl)cyclopentane

To a solution of 1α-((2α,5β-bis(3,4,5-trimethoxyphenyl)cyclopentyl)oxy)-N,N-dimethylacetamide (135 mg, 0.27 mmoles) in THF (4 ml) cooled in an ice bath was added $LiAlH_4$ (35 mg, 0.92 mmole). The suspension was stirred at room temperature in a $N_2$ atmosphere for 3 hours. It was then heated at 55° for 1 hour. After cooling in an ice bath, $H_2O$ (35 μl) was added cautiously followed by 15% NaOH (35 μl) and $H_2O$ (105 μl). The suspension was stirred at room temperature for 30 minutes. The solid was filtered and washed with THF. The filtrate and washes were dried ($K_2CO_3$) and evaporated in vacuo to give 121 mg of a colorless oil. This material was dissolved in $Et_2O$ (15 ml) and extracted with 1N HCl (three times). The combined acidic extracts were washed with $Et_2O$ and basified with 50% NaOH. The cloudy solution was extracted with $CH_2Cl_2$ (three times), and the combined extracts were washed with water and saturated brine and dried ($K_2CO_3$). Evaporation in vacuo gave 112 mg of a colorless oil. This material was purified by preparative TLC (silica gel; $CHCl_3$, acetone, $Et_2NH$; 10:4:1) to give 78 mg of 1α-N,N-dimethyl-aminoethoxy-2α,6β-bis(trimethoxyphenyl)cyclopentane as a colorless syrup.

NMR ($CDCl_3$: δ 6.58, 6.52 (s, 2H each, ArH), 3.74-3.90 (ms, 19H, ArOCH_3+C$\underline{H}$OCH_2), 3.00-3.50 (m, 6H, ArC$\underline{H}$+OCH_2CH_2N), 2.11 (s, 6H, N(CH_3)_2).

EXAMPLE 15

Cyclization of Dimethyl 2-(4-ethoxy-3-methoxy-5-n-propylthiophenyl)-5-(3,4,5-trimethoxyphenyl)-1,6-hexamedioate with KH A mixture of KH (3.70 g, 35% dispersion, 32.3 mmoles, washed (3×10 ml) with THF) and dimethyl 2-(4-ethoxy-3-methoxy-5-n-propylthiophenyl)-5-(3,4,5-trimethoxyphenyl)-1,6-hexanedioate (8.19 g, 14.5 mmoles) in THF (47 ml) was stirred at room temperature in a $N_2$ atmosphere for 4 hours. The brown suspension was cooled to −60° and 1.9 ml of HOAc was added with vigorous stirring. The yellow suspension was warmed to 0° with an ice bath and diluted with $H_2O$ (30 ml). The mixture was extracted with $Et_2O$ (3×). The combined $Et_2O$ extracts were washed with $H_2O$ (2×) and saturated NaCl solution and dried (mgSO_4). Evaporation in vacuo gave a quantitative yield of a mixture of regio-and stereoisomers of the cyclic keto ester 2. Mass spec: m/e 532 (M+).

EXAMPLE 16

Cyclization of Dimethyl 2-(4-ethoxy-3-methoxy-5-n-propylthiophenyl)-5-(3,4,5-trimethoxyphenyl)-1,6-hexamedioate with HN(SiMe_2)_2

A solution of dimethyl 2-(4-ethoxy-3-methoxy-5-n-propylthiophenyl)-5-(3,4,5-trimethoxyphenyl)-1,6-hexamedioate (564 mg, 1 mmole) in THF (2.0 ml) was added over 9 minutes to a solution of KN(SiMe_3)_2(4.0 ml, 0.5 M in toluene) in THF (2.0 ml) cooled in an ice bath in a N₂ atmosphere. The brown suspension was allowed to warm to room temperature and stirred for 45 minutes. It was cooled to −60° and HOAc (150 μl) was added. The reaction was worked up as in Example 15 to give a quantitative yield of the same mixture of regio- and stereoisomers of 2 as in Example 15. Other bases such as NaN(SiMe₃)₂, KOt-Bu, NaCHp₃ wherein Ph represents phenyl or substituted phenyl, LiN(iPr)₂, NaH, LiH, NaNH₂, NaNH₂, KNH₂, t-BuLi and LiNH₂ may also be used. And solvents other than THF, for example Et₂O, R*OCH₂CH₂OR* wherein R* represents methyl or ethyl, HMPA, DMF, toluene and benzene may also be used.

EXAMPLE 17

Trans-2-(4-Ethoxy-3-methoxy-5-n-propylthiophenyl)- 5-(3,4,5-trimethoxyphenyl)cyclopentanone (7)

A solution of the mixture of cyclic keto esters 2(7.71 g, 14.5 moles) and LiCl (1.23 g, 29 mmoles) in DMSO (24 ml) and H₂O (0.24 ml) n a N₂ atmosphere was placed in an oil bath heated to 185°. After 20 minutes CO₂ evolution stopped, and the red-brown mixture was cooled rapidly and poured into H₂O (200 ml) acidified with a few mls of 2N HCl. After extraction with Et₂O (3×), the combined extracts were washed with H₂O (3×) and saturated NaCl solution and dried (MgSO₄). Evaporation of the Et₂O in vacuo gave a quantitative yield of crude trans-2-4-ethoxy-3-methoxy-5-n-propylthiophenyl)-5-(3,4,5-trimethoxyphenyl)-cyclopentanone. IR 1740 cm⁻¹ (c=o). NMR: w 1.03 (t, 3H, CH₃(CH₂)₂S), 1.40 (t, 3H, CH₃CH₂O), 2.87 (t, 2H, SCH₂), 4.06 (q, 2H, OCH₂), 6.47 (s, 2H, ArH); 6.66, 6.72 (d, 1H each, ArH). Other salts such as Me₄NCl, LiI, BiBr, LiOAc, Me₄NOAc, NaCN, KCN, NaCl, KCl and NaBr may also be used. Other solvents besides DMSO such as HMPA, DMF and H₂O can also be used.

The decarbomethoxylation can also be carried out by the following combination of reagents:

1. aqueous HBr, reflux.
2. LiI, γ-collidine, reflux.
3. 3-quinuclidinol, o-xylene, reflux.
4. Al₂O₃, dioxane-H₂O, reflux.
5. B₂O₃, 150°.
6. B(OH)₃, 150°-170°.

EXAMPLE 18

(1β, 2β, 5α)-2-(4-Ethoxy-3-methoxy-5-n-propylthiophenyl)-5- (3,4,5-trimethoxyphenyl)cyclopentanol (5) and (1α, 2β, 5α)-2-(4-Ethoxy-3-methoxy-5-n-propylthiophenyl)-5- (3,4,5-trimethoxyphenyl)cyclopentanol (4)

To a solution of crude trans-2-(4-ethoxy-3-methoxy-5-n-propylthiophenyl)-5-(3,4,5-trimethoxyphenyl)cyclopentanone (6.87 g, 14.5 mmoles) in MeOH (230 ml) was added at room temperature NaBH₄ (1.64 g, 43.4 mmoles) in several portions over 5 minutes. The solution was stirred at room temperature in a N₂ atmosphere for 21 hours and most of the MeOH removed in vacuo. The residue was suspended in H₂O and extracted with Et₂O (4×). The combined extracts were washed with H₂O (3×) and saturated NaCl solution and dried (MgSO₄). The residue after evaporation of the Et₂O in vacuo was filtered through a 9.5×11 cm column of silica gel (E. Merck, Kriselgel 60 ) with (1:1) EtOAc-hexane (21). Evaporation in vacuo gave 6.12 g of a crude mixture of cyclopentanols. Separation by HPLC on a Prep 500 with silica gel and 2:1 hexane-EtOAc gave 2.27 g (33% from 1) of 1β, 2β, 5α)-2-(4-ethoxy-3-methoxy-5-n-propylthiophenyl)-5-(3,4,5-trimethoxyphenyl)cyclopentanol (5, eluted first).

NMR: δ 1.04 (t, 3H, CH₃(CH₂)₂S), 1.42 (t, 3H, CH₃CH₂O), 2.90 (t, 2H, CH₂S), 4.08 (q, 2H, OCH₂), 6.55 (s, 2H, ArH), 6.67, 6.77 (s, 1H each, ArH) and 1.41 g (20% from 1) of 1a, 2β, 5α)-2-(4-ethoxy-3-methoxy-5-n-propylthiophenyl)-5-(3,4,5-trimethoxyphenyl)cyclopentanol (4, eluted last).

NMR: δ 1.05 (t, 3H, CH₃(CH₂)₂S), 1.41 (t, 3H, OCH₂CH₃), 2.91 (t, 2H, CH₂S), 4.08 (q, 2H, OCH₂), 6.52 (s, 2H, ArH), 6.70, 6.79 (s, 1H each, ArH).

Other reducing agents, e.g., LiAlH₄, LiAl(OMe)₃H, LiAl(Ot-Bu)₃H, LiBH₄, LiCNBH₃, NaAl(OCH₂C-H₂OMe)₂H₂, NaBH₄.AnCl₂, LiBet₃H, LiB(sec-Bu)₃H, LiB(isoamyl)₃H, KB(sec-Bu)₃H, KB(isoamyl)₃H, R and S-Alpine Hydride®, LiAlH₄/R or S-Me₂CH(NH₂)C(Ph)₂(OH), LiAlH₄/R or S-Me₂NCH₂CH(CH₃)COPh)(CH₂Ph)(OH),

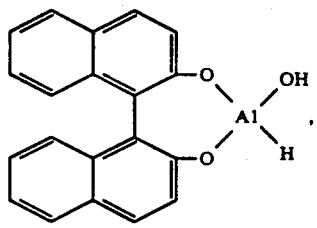

B₂H₆, 9-BBN and NB-Enantride may also be used

EXAMPLE 19

(1α-((2β,-(4-Ethoxy-3-methoxy-5-n-propylthiophenyl)- 5α-(3,4,5-trimethoxyphenyl)cyclopentyl)oxy)acetamide (6)

To a solution of (1α, 2β, 5α)-2-(4-ethoxy-3-methoxy-5-n-propylthiophenyl)-5-(3,4,5-trimethoxyphenyl)cyclopentanol (4) (1.22 g, 2.56 mmoles) in DMSO (5 ml) in a N₂ atmosphere at room temperature was added dropwise over 5 minutes 2.82 ms of 1.0 M K+DMSO⁻ in DMSO. After 10 minutes ethyl bromoacetate (0.37 ml, 3.34 mmoles) was added all at once with vigorous stirring. After 20 minutes at room temperature, the reaction was diluted with H₂O and extracted with ether (3×). The combined ether extracts were washed with H₂O (3×) and saturated NaCl solution and dried (MgSO₄). The residue from evaporation of the ether in vacuo was chromatographed on Prep 500 with silica gel and 2:1 hexane-EtOAc to give 0.42 g of ethyl 1α-((2β-(4-ethoxy-3-methoxy-5-n-propylthiophenyl)-5α-(3,4,5-trimethoxyphenyl)cyclopentyl)oxy)acetate.

NMR: δ 1.04 (t, 3H, CH₃(CH₂)₂S), 1.14 (t, 3H, CO₂CH₂CH₃), 1.41 (t, 3H, OCH₂CH₃), 2.90 (t, 2H, CH₂S), 3.62 (s, 2H, CH₂CO₂), 4.06 (q, 4H, CO₂CH₂, OCH₂), 6.61 (s, 2H, ArH), 6.74, 6.78 (d, 1H each, ArH) and 0.54 g of recovered starting cyclopentanol.

Ethyl 1α-((2β-(4-ethoxy-3-methoxy-5-n-propylthiophenyl)-5α-(3,4,5-trimethoxyphenyl)cyclopentyl)oxy)acetate(414 mg, 0.74 mmole) was dissolved in 40 ml of MeOH saturated with NH₃ at 0°, and the solution allowed to stand at room temperature for 17 hours. The NH₃and MeOH were evaporated in vacuo to give 375 mg of 1α-((2β-(4-ethoxy-3-methoxy-5-n-propylthiophenyl)-5α-(3,4,5-trimethoxyphenyl)cyclopentyl)oxy)acetamide (6).

NMR: δ 1.05 (t, 3H, CH₃((CH₂)₂S), 1.42 (t, 3H, OCH₂CH₃), 2.90 (t, 2H, SCH₂), 3.61 (d, 2H, CH₂CONH₂), 4.07 (q, 2H, OCH₂), 5.02, 5.79 (br s, 1H each, NH₂), 6.54 (s, 2H, ArH), 6.62, 6.74 (d, 1H each, ArH).

EXAMPLE 20

1α((2β-(4-Ethoxy-3-methoxy-5-n-propylsulfonyl-phenyl)-5α-(3,4,5-trimethoxyphenyl)cyclopentyl)oxy)-acetamide (7)

To a solution of 1α-((2β-(4-ethoxy-3-methoxy-5-n-propylthiophenyl)5α-(3,4,5-trimethoxyphenyl)cyclopentyl)oxy)acetamide (370 mg, 0.69 mmoles) in CH₂Cl₂ (4.0 ml) was added at room temperature 350 mg (1.62 mmoles) of m-chloroperbenzoic acid (80%). After stirring at room temperature for 3 hours, the solid m-chlorobenzoic acid was filtered and washed with CH₂Cl₂(3×1 ml). The filtrate was diluted with CH₂Cl₂, washed with 0.2 N NaOH, water and saturated NaCl solution and dried (MgSO₄). Evaporation in vacuo and purification of the residue by column chromatography on silica gel with 3:1 EtOAc-hexane gave 325 mg of 1α((2β-(4-ethoxy-3-methoxy-5-n-propylsulfonyl-phenyl)-5α-(3,4,5-trimethoxyphenyl)cyclopentyl)oxy)acetamide.

NMR: δ 1.02 (t, 3H, CH₃(CH₂)₂S), 1.46 (t, 3H, CH₃CH₂O), 3.57 (d, 2H, CH₂CONH₂), 4.23 (dq, 2H, OCH₂), 5.08, 5.79 (br, s, 1H each, NH₂), 6.56 (s, 2H, ArH), 7.03, 7.41 (d, 1H each, ArH).

The following compounds were prepared by the same or similar methods to those in Examples 15–20.

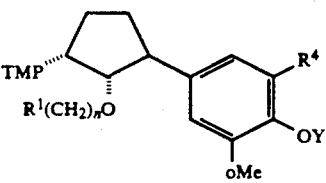

| (CH₂)ₙR¹ | R⁴ | Y | NMR (δ(ppm)) |
|---|---|---|---|
| CH₂CH≡CH | SO₂Me | Et | 1.46(t, 3H, CH₃CH₂O), 2.29 (t, 1H, ≡CH), 3.28(s, 3H, SO₂Me), 3.7(m, 2H, CH₂C≡), 4.23(q, 2H, OCH₂), 6.58(s, 2H, ArH), 7.18, 7.46(d, 1H each, ArH). |
| CH₂CO₂H | SO₂nPr | Et | 1.02(t, 3H, CH₃(CH₂)₂), 1.46 (t, 3H, CH₃CH₂O), 3.61(d, 2H, CH₂CO₂), 4.22(dq, 2H, OCH₂), 6.56(s, 2H, ArH), 7.09, 7.41(d, 1H each, ArH). |
| CH₂C(O)NHEt | SO₂nPr | Et | 0.87(t, 3H, CH₃CH₂N), 1.02 (t, 3H, CH₃(CH₂)₂), 1.46(t, 2H, CH₃O), 3.02(dq, 2H, CH₃CH₂N), 3.56(d, 2H, CH₂CO), 4.22(dq, 2H, OCH₂CH₃), 6.56(s, 2H, ArH), 7.03, 7.40(d, 1H each, ArH). |
| CH₂CH₂OH | SO₂nPr | Et | 1.01(t, 3H, CH₃(CH₂)₂), 1.46 (t, 3H, CH₃CH₂O), 4.22(q, 2H, OCH₂), 6.56(s, 2H, ArH), 7.08, 7.45(d, 1H each, ArH). |
| CH₂CH₂CONH₂ | SO₂nPr | Et | 1.01(t, 3H, CH₃(CH₂)₂), 1.46 (t, 3H, CH₃CH₂O), 4.23(q, 2H, OCH₂), 4.95, 5.67(br s, 1H each, CONH₂), 6.54(s, 2H, ArH), 7.06, 7.42(d, 1H each, ArH). |
| CH₂CONH₂ | SOnPr | Et | 1.06(t, 3H, CH₃(CH₂)₃), 1.36 (t, 3H, CH₃CH₂O), 3.45–3.61 (m, 2H, CH₂CO), 4.26(m, 2H, CH₂O), 5.20, 5.82(br s, 1H each, NH₂), 6.55(s, 2H, ArH), 6.88, 7.03(s, 1H each, ArH). |
| CH₂C(O)N(CH₂Ph)₂ | SO₂nPr | Et | 1.00(t, 3H, CH₃(CH₂)₂), 1.46 (t, 3H, CH₃CH₂O), 4.21(m, 2H, OCH₂), 6.32(s, 2H, ArH), 6.86–7.4(m, 10H, Ph H's), 7.39(d, 1H, ArH). |
| CH₂CH=CH₂ | SCH₃ | nPr | 4.89, 5.03(s, d, 2H, =CH₂), 5.66(m, 1H, —CH=). |

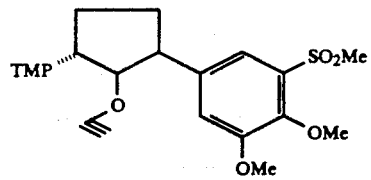

1.46(t, 3H, CH₃CH₂O), 2.31 (t, 1H, ≡CH), 3.27(s, 3H, SO₂Me), 4.24(q, 2H, OCH₂), 6.54(s, 2H, ArH), 7.22, 7.45 (d, 1H each, ArH).

This invention also relates to a method of treatment for patients (or mammalian animals raised in the dairy, meat, or fur industries or as pets) suffering from disorders or diseases which can be attributed to PAF as previously described, and more specifically, a method of treatment involving the administration of the PAF antagonists of formula (I) as the active constituents.

Accordingly, the compounds of Formula (I) can be used among other things to reduce pain and inflammation, to correct respiratory, cardiovascular, and intravascular alterations or disorders, and to regulate the activation or coagulation of platelets, to correct hypotension during shock, the pathogenesis of immune complex deposition and smooth muscle contractions.

For the treatment of inflammation such as rhumatoid arthritis, osteoarthritis and eye inflammation, cardiovascular disorder, asthma, shock syndrome or other diseases mediated by the PAF, the compounds of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in the form suitable for oral use, for example, as tablets, troches, lozenges, aqueous or oily suspension, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspension. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters for partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example a solution in 1,3-butane diol. Among the acceptable vehicle and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed.

Dosage levels of the order of from about 0.1 mg to about 140 mg per kilogram of body weight per day are useful in the treatment of the above-indicated conditions (about 0.5 mg to about 7 gms. per patient per day). For example, inflammation may be effectively treated by the administration of from about 0.01 to 50 mg of the compound per kilogram of body weight per day (about 1.0 mg to about 3.5 gms per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

It has been found that the compounds of formula (I) exhibit antagonistic activities with respect to PAF. They inhibit in vitro PAF-induced functions in both the cellular and tissue levels by changing the PAF binding to its specific receptor site. This ability to inhibit the PAF binding to its specific receptor binding site on rabbit platelet plasma membranes was measured by an assay recently developed by us.

The inhibition of $H^3$-PAF binding to the rabbit platelet plasma membrane by a PAF antagonist of Formula (I) was determined by isotopic labeling and filtration techniques. Generally, a series of Tris-buffered solutions of the selected antagonist at predetermined concentrations were prepared. Each of these solutions contains 1 pmole of $^3$H-PAF, a known amount of the test antagonist, and a sufficient amount of the pH 7.5 Tris-buffer solution (10 mM Tris, 0.25% bovine serum albumin, and 150 mM NaCl per ml water) to make the final volume of 1 ml. After adding into a set of test tubes each with 100 μg of the platelet plasma membrane suspension (S. B. Hwang, et al., *Biochemistry*, Vol. 22, pp. 4756–4763, 1983) and one of the Tris-buffer solutions described above, the resulting mixture in each test tube was incubated at 0° C. for about one hour or until the reaction was complete. Two control samples, one of which ($C_1$) contains all the ingredients described above except the antagonist and the other ($C_2$) contains $C_1$ plus a 1000-fold excess of unlabeled PAF, were also prepared and incubated simultaneously with the test samples. After the incubation was completed, the contents of each test tube were filtered under vacuo through a Whatman GF/C fiberglass filter and the residue washed rapidly several times with a total of 20 ml cold (0°–5° C.) Tris-buffer solution. Each washed residue was then suspended in 10 ml scintillation solution (Aquasol 2, New England Nuclear, Conn.) and the radioactivity was counted in a Packard Tri-Carb 460CD Liquid Scintillation System. Defining the counts from a test sample as "Total binding with antagonist"; the counts from the control sample $C_1$, as "Total binding $C_1$"; and the counts from the control sample $C_2$ as "non-specific binding $C_2$", the percent inhibition of each test antagonist can be determined by the following equation:

$$\% \text{ Inhibition} = \frac{(\text{Total binding } C_1) - \left(\begin{array}{c}\text{Total binding} \\ \text{with antagonist}\end{array}\right)}{\text{Specfic binding}} \times 100$$

$$\text{Specific binding} = (\text{Total binding } C_1) - (\text{non-specific binding } C_2)$$

The antagonistic activity of the compounds of structural formula (I) is illustrated in the following tables (A) and (B):

TABLE (A)

| R | PAF Receptor Binding Inhibition $IC_{50}$(nM) (rabbit) | Percent Inhibition |
|---|---|---|
| $-O-CH_2-C\equiv CH$ | 1.0 | |
| $-O-CH_2-COOC_2H_5$ | 3.6 | |
| $-O-CH_2-CH=CH_2$ | 4.8 | |
| $=NOCH_3$ | 5.0 | |
| $=NOH$ | 5.8 | |
| $-OCH_3$ | 8.3 | |
| $-O-\text{cyclopropylmethyl}$ | 19 | |
| H | 20 | |
| $-O-CH_2CH_2CH_3$ | 30 | |
| $-O-CH_2CH_2CH_2CH_3$ | 30 | |
| $-O-CH_2C_6H_5$ | 48 | |
| $-O-CO-CH_3$ | 100 | |
| $-O-CH_2CH_2-OCH_3$ | 100 | |
| $-O-CH_2CH_2-N(CH_3)_2$ | 100 | |
| $-OH$ | | 84% at 500 nM |
| $-O-CH_2-CON(CH_3)_2$ | | 23% at 300 nM |
| $-O-CH_2-COOH$ | | 16% at 300 nM |

TABLE (B)

| R | $R^4$ | PAF Receptor Binding Inhibition $IC_{50}$(nM) (rabbit) | Percent Inhibition |
|---|---|---|---|
| ◄OCH₃ | SO₂CH₃ | 4.3 | |
| ◄OCH₃ | SOCH₃ | 18 | |
| ◄OCH₃ | SCH₃ | 15 | |
| ◄OH | SCH₃ | | 23% at 300 nM |
| ⋯OCH₃ | SO₂CH₃ | 3.8 | |
| ⋯OCH₃ | SOCH₃ | 9.3 | |
| ⋯OCH₃ | SCH₃ | 3 | |
| ⋯OH | SCH₃ | | 38% at 300 nM |
| ⋯OCH₃ | Br | 47 | |
| ⋯OCH₃ | CN | 91 | |
| ◄OCH₃ | CN | 21 | |

TABLE (B)-continued

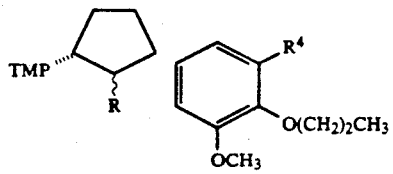

| R | R⁴ | PAF Receptor Binding Inhibition IC$_{50}$(nM) (rabbit) | Percent Inhibition |
|---|---|---|---|
| ⋯OCH$_3$ | (CO)NH$_2$ | 124 | |
| ◂OCH$_3$ | (CO)NH$_2$ | 47 | |

What is claimed is:

1. A compound of the formula:

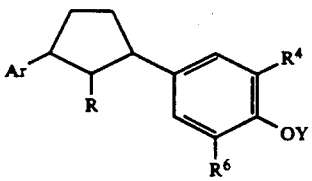

wherein

R is O—(CH$_2$)$_n$—R$^1$, wherein n is an integer from 1 to 6; and

R$^1$ is H, C$_{1-6}$ alkyl or hydroxy substituted C$_{1-6}$ alkyl, C$_{1-6}$ alkenyl, C$_{3-8}$ cycloalkyl, C$_{1-6}$ alkynyl, OR$^2$, halo, perhalo C$_{1-6}$ alkyl, phenyl or substituted phenyl as defined below;

R$^2$ is H, C$_{1-8}$ alkyl, C$_{3-8}$ cycloalkyl, phenyl C$_{1-3}$ alkyl, perhalo C$_{1-4}$ alkyl and Ar and Ar$^1$ independently are: phenyl or substituted phenyl of formula $$\begin{array}{c} R^7 \\ R^6 \end{array} \bigcirc \begin{array}{c} R^3 \\ R^4 \\ R^5 \end{array}$$

wherein R$^3$-R$^7$ independently represents H; R$^2$; —OY wherein Y is C$_{1-6}$ alkenyl, C$_{1-6}$ alkynyl, —CH$_2$—C$_{3-8}$ cycloalkyl, —CH$_2$—CH(OH)—CH$_2$OH; —SR$^2$; —SO—R$^2$; —SO$_2$—R$^2$; —OCF$_3$; —SCF$_3$; —SO—CF$_3$; —SO$_2$—CF$_3$; —OCH$_2$OCH$_3$; halo with the proviso that Ar and Ar$^1$ are not simultaneously the same and that at least one of R$^3$-R$^7$ contains a sulfur.

2. The compound of claim 1 wherein the compound is of formula $$Ar \diagdown \bigcirc \diagup \begin{array}{c} R^4 \\ OY \\ R^6 \end{array}$$

wherein Ar is 3,4,5 trimethoxyphenyl.

3. Compound of claim 2 wherein R$^4$ is selected from the group consisting of
R$^4$ is
(a) SO$_2$—C$_{1-6}$ alkyl;
(b) SO—C$_{1-6}$ alkyl;
(c) S—C$_{1-6}$ alkyl; or
(d) Br.

4. A pharmaceutical composition for treating a disease or a disorder mediated by PAF comprising a pharmaceutical carrier and a therapeutically effective amount of a compound according to claim 1.

5. A pharmaceutical composition for treating a disease or a disorder mediated by PAF comprising a pharmaceutical carrier and a therapeutically effective amount of a compound according to claim 2.

6. A method for the treatment of a disease or a disorder mediated by PAF comprising administering to a mammalian species in need of the treatment a therapeutically effective amount of a compound according to claim 1.

7. A method for the treatment of a disease or a disorder mediated by PAF comprising administering to a mammalian species in need of the treatment a therapeutically effective amount of a compound according to claim 2.

8. A compound of claim 2 wherein
Ar is 3,4,5 trimethoxyphenyl;
R is —OCH$_2$CH$_2$OH;
R$^4$ is SO$_2$-n-propyl;
Y is ethyl; and
R$^6$ is methoxy.

* * * * *